(12) United States Patent
Fujimaki et al.

(10) Patent No.: US 7,692,787 B2
(45) Date of Patent: Apr. 6, 2010

(54) CHIP FOR RAMAN SCATTERING ENHANCEMENT AND MOLECULAR SENSING DEVICE INCLUDING THE CHIP

(75) Inventors: Makoto Fujimaki, Tsukuba (JP); Junji Tominaga, Tsukuba (JP); Yasuhiko Iwanabe, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 11/883,405

(22) PCT Filed: Jan. 26, 2006

(86) PCT No.: PCT/JP2006/301197

§ 371 (c)(1),
(2), (4) Date: May 23, 2008

(87) PCT Pub. No.: WO2006/080382

PCT Pub. Date: Aug. 3, 2006

(65) Prior Publication Data

US 2009/0027668 A1    Jan. 29, 2009

(30) Foreign Application Priority Data

Jan. 31, 2005    (JP) .............................. 2005-022698

(51) Int. Cl.
*G01J 3/44* (2006.01)
*G01N 21/65* (2006.01)
(52) U.S. Cl. ...................................... 356/301
(58) Field of Classification Search .................. 356/301
See application file for complete search history.

(56) References Cited

U.S. PATENT DOCUMENTS 5,017,007 A    5/1991    Milne et al.

(Continued)

FOREIGN PATENT DOCUMENTS

JP    4-506999    12/1992

(Continued)

OTHER PUBLICATIONS

Brioude, A. "Raman spectroscopy of sol-gel ultrathin films enchanced by surface Plasmon polaritons", J. of Applied Phys. 88(11):6187-6191 (2000).

(Continued)

*Primary Examiner*—F. L Evans
(74) *Attorney, Agent, or Firm*—Fish & Richardson P.C.

(57) ABSTRACT

The present invention aims to provide a chip applied to a molecular sensing device which carries out Raman spectroscopic analysis utilizing Raman scattering enhancement due to plasmons, and that achieves higher sensitivity and stability of its sensing sensitivity and miniaturization, and to provide a molecular sensing device including the chip. As the chip for Raman scattering enhancement applied to the molecular sensing device using the Raman spectroscopic analysis, which has an excitation light source for Raman scattering, a chip for Raman scattering enhancement and a photodetector for observing the Raman scattering, the present invention employs a chip having a molecular detecting element in which a transparent protection material thin film 32 composed of a dielectric material thin film or semiconducting material thin film is formed on a thin film 31 containing the noble metal oxide, and utilizes the Raman scattering enhancement by the thin film containing the noble metal oxide.

16 Claims, 21 Drawing Sheets

U.S. PATENT DOCUMENTS

| | | | |
|---|---|---|---|
| 6,707,549 B2 | 3/2004 | Tominaga et al. | |
| 7,384,792 B1 * | 6/2008 | Wang et al. | 436/165 |
| 2002/0145735 A1 * | 10/2002 | Tominaga et al. | 356/301 |
| 2004/0048075 A1 | 3/2004 | Tominaga et al. | |
| 2006/0034729 A1 * | 2/2006 | Poponin | 422/82.05 |

FOREIGN PATENT DOCUMENTS

| | | |
|---|---|---|
| JP | 2000-356587 | 12/2000 |
| JP | 2002-277397 | 9/2002 |
| JP | 2004-20822 | 1/2004 |

OTHER PUBLICATIONS

Inouye et al., "Near-field scanning optical microscope using a metalized cantilever tip for nanospectoscopy", Proc. SPIE, 3791 Abstract (1999).

Fuji et al., "A Near-Field Recording and Readout Technology Using a Metallic Probe in an Optical Disk", Jpn. J. Appl. Phys. 39:980-981 (2000).

Büchel et al., "Sputtered silver oxide layers for surface-enhanced Raman spectroscopy", Applied Physics Letter 79(5):620-622 (2001).

* cited by examiner

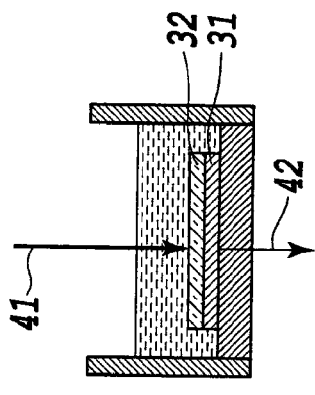
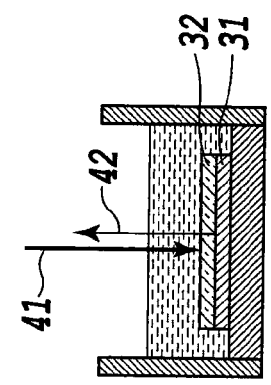
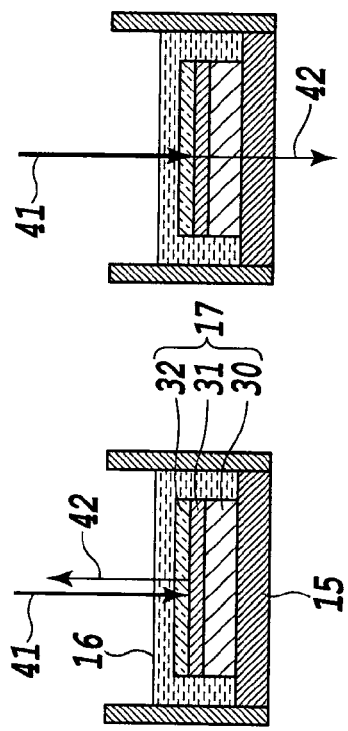
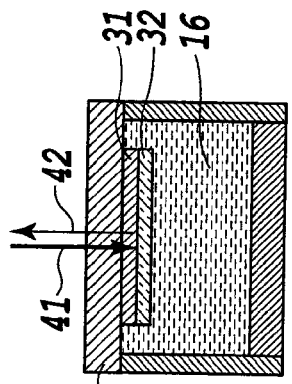
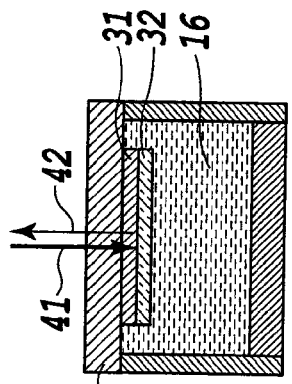
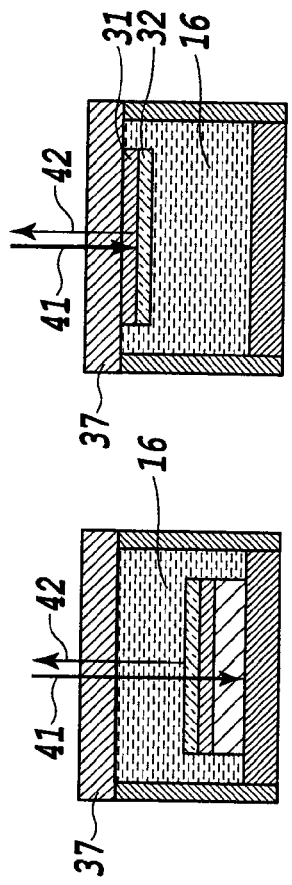
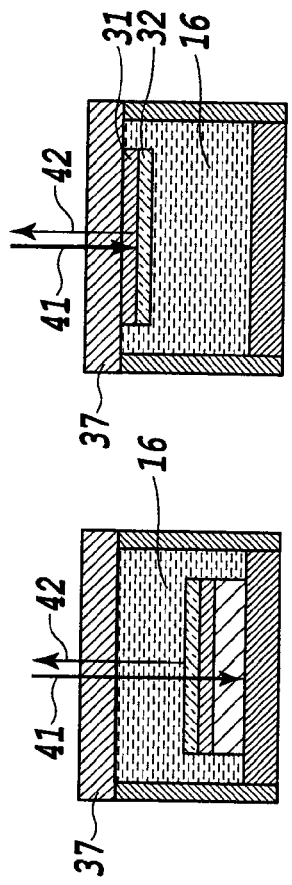
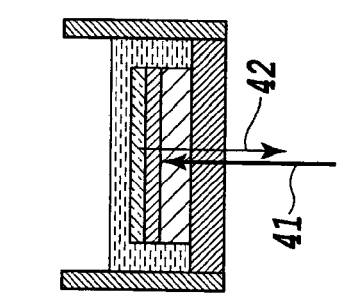
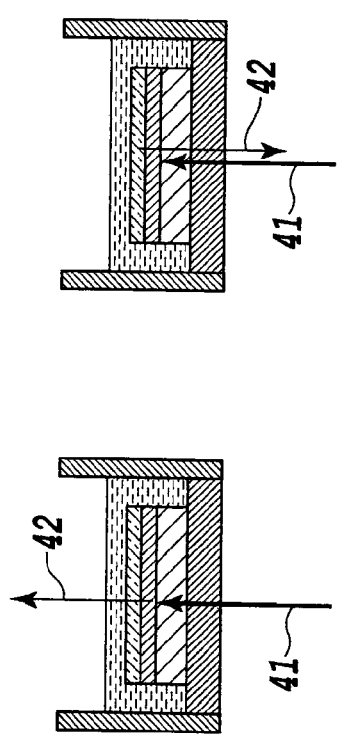
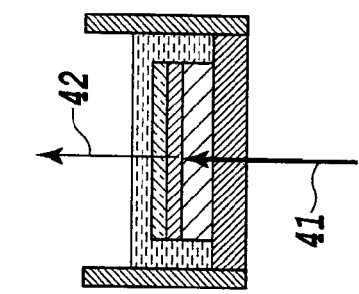

CHIP FOR RAMAN SCATTERING ENHANCEMENT AND MOLECULAR SENSING DEVICE INCLUDING THE CHIP

TECHNICAL FIELD

The present invention relates to a chip for Raman scattering enhancement, which is used as a sensor of a molecular sensing device (molecular sensor) for sensing molecules by Raman spectroscopic analysis, and a molecular sensing device including the chip.

BACKGROUND ART

Enhancement of Raman scattered light (Raman scattering enhancement) using plasmons generated on a metal thin film surface or metal particle surface is know as surface enhanced Raman scattering (SERS), and applications to detection and identification of various materials have been reported. For example, J. Appl. Phys., Vol. 88, No. 11, pp. 6187-6191 (2000) describes Raman spectroscopic analysis utilizing electric field enhancement by surface plasmon-polariton. In this paper, Raman spectroscopic analysis of a $TiO_2$ thin film existed on an Ag thin film is carried out using the surface plasmon resonance of the silver thin film formed on a glass substrate. Such Raman scattering enhancement using the surface plasmon-polariton caused by the metal thin film must use a total reflection prism. This presents a problem of complicating a device configuration because of an increase in the scale of the device due to using the total reflection prism, and because of the need of fixing the incident angle of an excitation laser beam.

The SERS can be induced not only by using the thin film, but also by using a metal of nano-scale. For example, throwing light to a metal needle with a nano-scale tip diameter, which is brought into contact with a specimen such as a molecule, makes it possible to enhance Raman scattered light from the molecule. A nearfield Raman microscope is also reported which carries out mapping of a specimen in a minute space by using such a nano-scale metal needle (Proc. SPIE., 3791, 40 (1999)). Although such an observation method is effective for specimen observation of a minute region, it is not applicable to simple and high speed specimen detection or specimen identification because of complicated formation of a microscopic metal needle or of a long time required for measurement in general.

Many reports have been made about SERS which uses noble metal particles such as island-shape particles of silver and so forth precipitated by a film deposition method in a vacuum or the like, or which uses noble metal colloids. However, the SERS using the noble metal particles presents a drawback of being it difficult to control variation in particle size or in particle spacing, and hence of having large variation in enhancement effect of Raman scattering enhancement. As for the case of SERS using the colloids, a drawback is known of being it difficult to carry out measurement or of being unable to obtain quantitativeness because of variation in enhancement effect of SERS owing to properties of a colloidal solution, particularly owing to pH of the solution, a material dissolved in the solution and so forth.

As molecular sensors that overcome the foregoing drawbacks in the molecular sensors employing the noble metal particles and that detect molecules stably and supersensitively, molecular sensors have been reported which employ silver particles formed at the time of thermal decomposition due to laser beam irradiation for a noble metal compound such as silver oxide (Jpn. J. Appl. Phys., 39, 980-981 (2000); Appl. Phys. Lett., 79, 620-622 (2001); and Japanese patent application laid-open No. 2002-277397).

Patent Document 1: Japanese patent application laid-open No. 2002-277397.

Non-Patent Document 1: J. Appl. Phys., Vol. 88, No. 11, pp. 6187-6191 (2000).

Non-Patent Document 2: Proc. SPIE., 3791, 40 (1999).

Non-Patent Document 3: Jpn. J. Appl. Phys., 39, 980-981 (2000).

Non-Patent Document 4: Appl. Phys. Lett., 79, 620-622 (2001).

DISCLOSURE OF THE INVENTION

Problems to Be Solved by the Invention

The molecular sensor, which uses silver particles formed by decomposition of a silver oxide by laser beam irradiation or the like, has a drawback of being lacking of sensitivity for detecting a specimen (such as molecules) with low Raman activity. In addition, a metal oxide like a silver oxide is high oxidative, and oxidizes the specimen or a solvent including the specimen, there by changing the quality thereof. As a result, it has a problem of detecting a material not included in the solvent originally.

Considering the foregoing problems, an object of the present invention is to provide a chip for molecular sensing device, which is applied to a molecular sensing device for carrying out Raman spectroscopic analysis utilizing Raman scattering enhancement due to plasmons, and which achieves higher sensitivity and stability of its sensing sensitivity and miniaturization, and to provide a molecular sensing device including the chip.

MEANS FOR SOLVING THE PROBLEMS

In the molecular sensing device using the Raman spectroscopic analysis, which has an excitation light source for Raman scattering, a chip for Raman scattering enhancement and a photodetector for observing the Raman scattering, the present invention employs as the chip for Raman scattering enhancement a chip having a molecular detecting element that has a dielectric material thin film or semiconducting material thin film formed on a thin film containing the noble metal oxide, and that utilizes the Raman scattering enhancement by the thin film containing the noble metal oxide.

EFFECT OF THE INVENTION

According to the present invention, it can detect molecules with higher sensitivity than the conventional molecular sensing device using the thin film containing the noble metal oxide (or noble metal oxide film). In addition, it can suppress a chemical reaction between the noble metal oxide and the molecules to be detected or a solution or gas containing the molecules to be detected, and can detect the molecules stably and at higher accuracy.

BRIEF DESCRIPTION OF THE DRAWINGS

FIG. 7 is views each showing a deposition example of a chip for Raman scattering enhancement, specimen, cell, excitation light incident direction and Raman scattered light detection direction;

Figure 1:
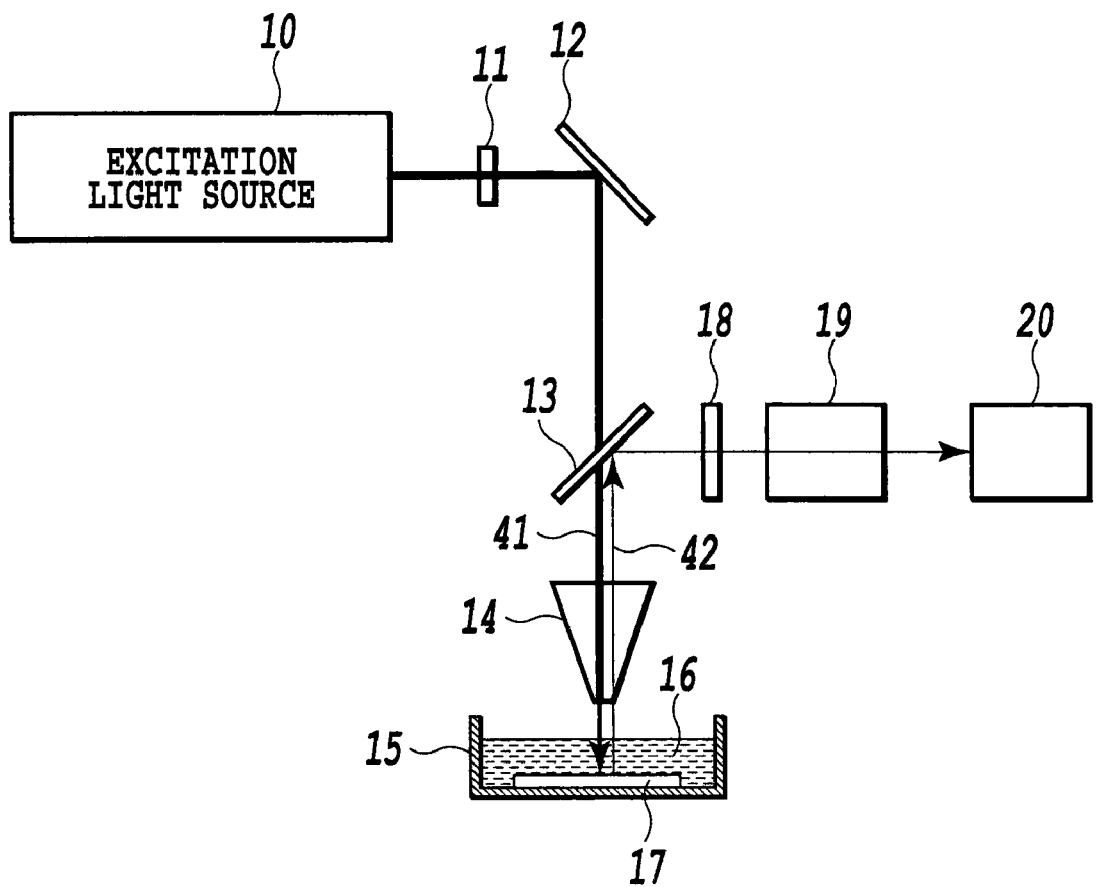
FIG. 1 is a diagram showing a configuration of a molecular sensing device in accordance with the present invention.

DESCRIPTION OF REFERENCE NUMERALS 10 excitation light source; 11 optical filter; 12 mirror; 13 half mirror; 14 objective lens; 15 container; 16 specimen; 17 chip for Raman scattering enhancement, 18 notch filter; 19 monochromator; 20 photo-detector; 30 substrate; 31 thin film containing a noble metal oxide; 32 dielectric material thin film or semiconducting material thin film; 33 particles containing a noble metal; 35 metal layer; 36 dielectric material thin film or semiconducting material thin film; 37 cap; 38 $TiO_2$ thin film layer; 39 $SiO_2$ thin film layer; 41 excitation light; and 42 Raman scattered light.

BEST MODE FOR CARRYING OUT THE INVENTION

A molecular sensing device in accordance with the present invention detects molecules by observing Raman scattered light from molecules to be detected. FIG. 1 is a diagram showing a configuration of the molecular sensing device in accordance with the present invention.

The light emitted from an excitation light source 10 for inducing Raman scattering is passed through an optical filter 11 to remove unnecessary emission lines and the like. After that, a mirror 12 changes an orientation of its optical alignment to guide to an objective lens 14. Excitation light 41 passing through the objective lens 14 is focused on a chip for Raman scattering enhancement 17 in accordance with the present invention, which will be described later, so that the chip is irradiated with the light. In this case, the chip for Raman scattering enhancement 17 is placed on the bottom of the container 15 for containing a specimen, and the container 15 contains the specimen (a solution containing the specimen in this case) 16. The chip for Raman scattering enhancement 17 is disposed in such a manner that a molecular detecting element, that is, a thin film layer containing a noble metal oxide and a dielectric material thin film layer or a semiconducting material thin film layer, faces upward. The specimen close to the surface of the chip for Raman scattering enhancement has its Raman scattered light intensity enhanced by the chip for Raman scattering enhancement 17. Since the Raman scattered light 42 includes reflected light or scattered light of the excitation light, a notch filter 18 eliminates them so that only the Raman scattered light is applied onto a monochromator 19. The monochromator 19 separates the Raman scattered light into its spectral components, and a photo-detector 20 detects them to carry out molecular sensing.

The above is only an example of the molecular sensing device, but any optical arrangements are applicable to the invention as long as they can carry out conventional Raman scattering spectroscopic analysis. For example, since the main purpose of the optical filter 11 is to eliminate the unnecessary light from the excitation light source 10 to prevent the unnecessary light from the excitation light source from entering in the signal to be observed, or to prevent the Raman scattered light due to the unnecessary light from entering in the photo-detector, the optical filter becomes unnecessary depending on the excitation light source used or on the Raman scattering signal to be observed. Besides, although the mirror 12 is used to achieve the optical alignment, it goes without saying that the mirror becomes unnecessary depending on the arrangement of the excitation light source, or a plurality of mirror can sometimes become necessary. In addition, an optical fiber is applicable to guide the excitation light. Although the objective lens 14 is effective for measuring a micro capacity specimen in a micro region, that is, for micro-observation, a large quantity of the specimen or a large region to be detected can obviate the need for the objective lens 14.

As for the Raman scattered light in FIG. 1, backward scattering (Raman scattering toward the side the excitation light enters) is observed. However, since the Raman scattering spreads in all directions, the observation is not limited to the backward observation, but can be achieved in any desired direction. FIG. 1 shows an example of the observation of the backward scattering. Accordingly, the optical alignment of the excitation light source laps over the optical alignment of the Raman scattered light. Thus, the Raman scattered light is directed to the photo-detector 20 by use of the half mirror 13. The reason for using the half mirror 13 is that if the mirror is a total reflection mirror, the excitation light is also totally reflected, and the excitation light cannot reach the specimen. Accordingly, if the direction of obtaining the Raman scattered light differs, the half mirror can be replaced by a mirror. Besides, it is obvious that the mirror becomes unnecessary depending on the placement of the photo-detector. In addition, just as the excitation light, the Raman scattered light can be guided to the photo-detector through an optical fiber.

The notch filter 18, which is used to remove the excitation light as described above, is also unnecessary when the signal to be observed is observed at a location separated from the excitation light in terms of energy. In addition, although the monochromator 19 is used for detecting the signal in FIG. 1, when the wavelength range of the signal to be observed is fixed, that is, when only a particular signal of particular molecules is observed to detect the presence or absence of the particular molecules, an optical filter can be used in place of the monochromator, and this enables simplification of the device. As the photo-detector 20, any types of conventionally used photo-detectors such as a CCD, photomultiplier tube and photodiode are applicable.

As described above, according to the present invention, any optical arrangements can be employed as long as they carry out conventional Raman spectroscopic analysis. Thus, the concrete configuration of the detecting device itself in accordance with the present invention is not limited in particular. However, it must include at least the excitation light source for exciting Raman scattering, the photo-detector for detecting the Raman scattered light and the chip for Raman scattering enhancement in accordance with the present invention without exception.

In FIG. 1, the observation was carried out with placing the chip for Raman scattering enhancement in accordance with the present invention on the bottom of the container of the specimen with facing upward, with filling the container with the specimen, and with irradiating the surface of the chip for Raman scattering enhancement with the excitation light. It is preferable that the arrangement be changed according to a subject to be detected. In addition, the sensing is possible without using the container of the specimen, but with only applying a coating of the specimen or mounting the specimen to or on the chip for Raman scattering enhancement. In other words, to carry out the sensing, it is enough that the specimen is brought into contact with or close at least to the surface (that is, on the molecular detecting element) of the chip for Raman scattering enhancement. As for the placement of the chip for Raman scattering enhancement and specimen, the direction of radiation of the excitation light source for Raman scattering and the direction of observation of the Raman scattered light, there are a variety of methods according to an arrangement of the chip for Raman scattering enhancement which will be described below. Thus, their description will be made after explaining the configuration of the chip for Raman scattering enhancement.

The chip for Raman scattering enhancement in accordance with the present invention is built by forming a thin film containing a noble metal oxide on part or all of the surface of a substrate, and by further forming on the surface of the thin film containing the noble metal oxide a transparent protection material thin film consisting of a dielectric material thin film, semiconducting material thin film or the like. As for the substrate, any solid state materials are applicable, and its shape can be chosen appropriately according to its use or application area.

It is consider that the molecular sensing device in accordance with the present invention creates the particles containing the noble metal from the noble metal oxide of the chip for Raman scattering enhancement, and detect the specimen by Raman spectroscopic analysis by utilizing the Raman scattering enhancement caused by the localized plasmons created near the surface of the particles. In other words, the molecular sensing device carries out the sensing of the molecules by forming the dielectric material thin film or semiconducting material thin film on the thin film containing the noble metal oxide, and then by creating the particles containing the noble metal from the noble metal oxide.

The generation of the particles containing the noble metal from the noble metal oxide can be performed by electromagnetic irradiation to or heating of the noble metal oxide, for example. As for the particulate generation reaction, which is also described in Japanese patent application laid-open No. 2002-277397, it is thought that the above particles containing the noble metal are formed by the reduction or decomposition of the noble metal oxide due to the electromagnetic irradiation or heating.

As for the noble metal oxide, although it is not particularly restricted as long as it can form the particles containing the noble metal in practice by the reduction or decomposition of the noble metal oxide due to the electromagnetic irradiation or heating as described above, such as silver, platinum or palladium, it is preferable to use a silver oxide. In addition, although the noble metal oxide can be a stoichiometric composition, it need not necessarily fulfill the stoichiometric composition, but its composition can be appropriately determined experimentally in such a manner as to increase the amount of the enhancement of the Raman scattering. For example, when using the silver oxide, the value x of $AgO_x$ is preferably in a range from 0.2 to 1.

The thin film containing the noble metal oxide is preferably formed by physical vapor deposition method or film deposition method in a vacuum. As the physical vapor deposition method, a sputtering method is preferable, and as the film deposition method in a vacuum, a vacuum vapor deposition method is preferable. The sputtering method can employ a material containing the noble metal oxide as a target, or carry out reactive sputtering using a noble metal target in an atmosphere including oxygen. If it employs the reactive sputtering, it can easily control the composition of the noble metal oxide, particularly the oxygen content, by controlling the flow rate of the oxygen gas and/or the oxygen partial pressure in the atmosphere. Accordingly, it can easily form the noble metal oxide with a composition enabling greater Raman scattering enhancement. The composition of the noble metal oxide, particularly the oxygen content, can also be adjusted by heat treatment during or after the thin film formation.

The film thickness of the thin film containing the noble metal oxide is about 1-500 nm, and preferably about 3-100 nm. As the film thickness becomes thinner, the size of the particles formed becomes smaller, and hence the intensity of the Raman scattered light becomes stronger. However, when the film becomes too thin, the particle diameters become too small, and the Raman scattering enhancement reduces on the contrary.

Figure 2:
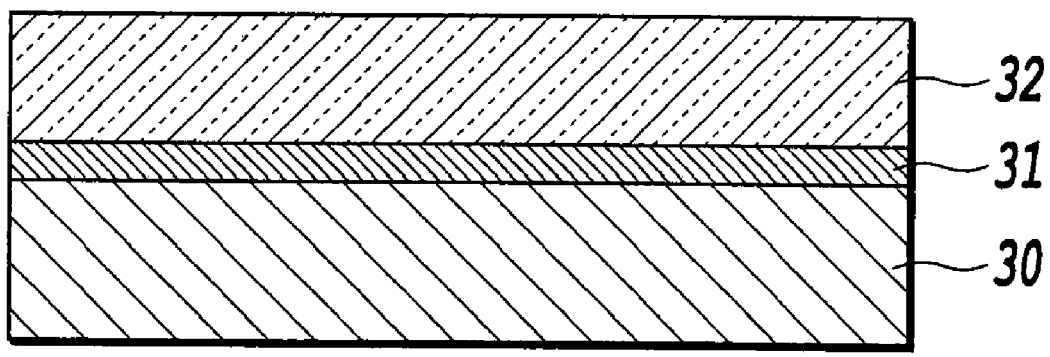
FIG. 2 is a schematic cross-sectional view showing a structure of a chip for Raman scattering enhancement in accordance with the present invention.

According to the present invention, a dielectric material thin film or semiconducting material thin film is further formed on the thin film containing the noble metal oxide which is formed as described above. FIG. 2 is a schematic cross-sectional view showing the most basic structure of the chip for Raman scattering enhancement in accordance with the present invention. As shown in FIG. 2, a substrate 30 is prepared, first. Then a thin film 31 containing the noble metal oxide is formed on the surface of the substrate 30 using the foregoing method. In addition, a dielectric material thin film or semiconducting material thin film 32 is formed on the thin film 31.

Figure 3:
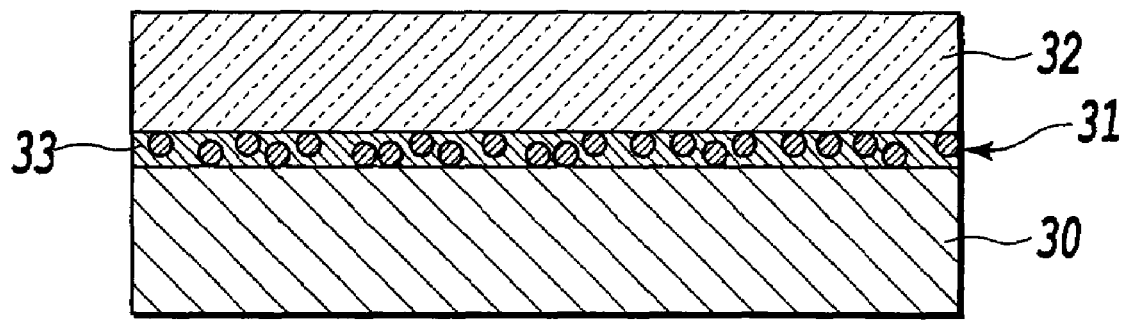
FIG. 3 is a schematic diagram showing a state in which particles containing a noble metal are formed in a thin film containing a noble metal oxide.

Thus forming the dielectric material thin film or semiconducting material thin film 32 will bring about the reduction or decomposition of the noble metal oxide, thereby forming particles 33 containing the noble metal. In the course of this, the particles 33 are formed in such a manner that they are enclosed in a dielectric or semiconductor. FIG. 3 shows this state schematically. The particles 33 enclosed in the dielectric or semiconductor in this way can change the wavelength range of the excitation light for bringing on the Raman scattering enhancement, thereby being able to achieve highly sensitive sensing using a variety of light sources.

This effect, the state of FIG. 3, will be described by way of example in which the noble metal particles are contained in spherical dielectric particles simulatively. Consider the case where silver particles are used as the noble metal particles, and silica glass is used as the dielectric material. When the diameter of the silver particle is 40 nm, and no silica glass is used, the wavelength range of the excitation light that enables the electric field enhancement efficiently by creating the localized plasmons is about 370 nm-430 nm. On the other hand, when the silver particles are enclosed in silica glass spheres with a thickness of 50 nm, the wavelength range of the excitation light can be shifted to about 430 nm-600 nm. In addition, using titanium dioxide instead of silica glass makes it possible to shift the excitation wavelength range to 500 nm-700 nm with the same thickness (50 nm).

Generally, although analysis using Raman scattering is an effective method of identifying molecules, if the laser beam irradiation for inducing the Raman scattering brings about light emission of the specimen or of a material containing the specimen such as a solvent, the Raman scattered light may be tricky to detect by the light emission. As for the Raman scattered light, its peak or waveform is always observed at a position having a fixed energy difference with reference to the excitation light energy. On the other hand, as for the light emission, its peak position often takes place in a fixed energy band regardless of the light source. In addition, the light emission can be restrained by selecting the light source. Consequently, the present method can vary the wavelength range of the excitation light that can generate the Raman scattering enhancement efficiently, and can suppress the hindrance to the measurement by the light emission by using appropriate light source in the wavelength range effective for the Raman spectroscopic analysis.

In this way, the present invention can broaden the scope of selection of the light source as compared with the prior art, and achieve more highly sensitive molecular sensing.

The dielectric particles or semiconductor particles containing the noble metal particles sometimes create the localized plasmons more intensely. As described above, the present invention is considered to be trying to create the dielectric particles or semiconductor particles containing the noble metal particles simulatively. This also contributes to the improvement of the sensor sensitivity.

In addition, a metal layer or a layer containing island-shape metal particles placed near the noble metal particles will be able to create the localized plasmons more strongly. Accordingly, the Raman scattering enhancement can be further increased and the sensitivity of the sensor can be further improved by forming the metal layer or the layer containing metal particles on the surface of the substrate, or by forming the substrate itself of a metal substantially. In this case, if the metal is a noble metal such as gold, silver, platinum and palladium, further improvement in the sensitivity can be expected.

Figure 4:
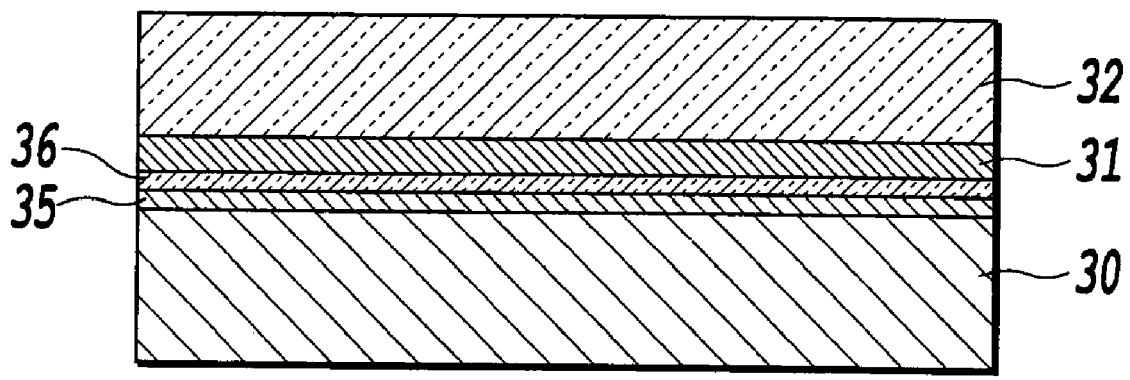
FIG. 4 is a schematic cross-sectional view showing another structure of a chip for Raman scattering enhancement in accordance with the present invention.

However, if the particles containing the noble metal formed of the layer containing the noble metal oxide is in direct contact with the substrate surface or with the metal of the substrate itself, the intensity of the localized plasmons can be weakened. Accordingly, the reduction in the intensity of the localized plasmons can be prevented by further forming a dielectric material thin film or semiconducting material thin film on the metal on the substrate surface to prevent the layer containing the noble metal oxide from making direct contact with the metal on the substrate surface. FIG. 4 illustrates an example of a chip for Raman scattering enhancement with such a structure. The chip for Raman scattering enhancement as shown in FIG. 4 has a structure of stacking on the substrate 30 a metal layer 35, a dielectric material thin film or semiconducting material thin film 36, the thin film 31 containing the noble metal oxide, and the dielectric material thin film or semiconducting material thin film 32.

In addition, the chip for Raman scattering enhancement in accordance with the present invention has an advantage of being able to circumvent the direct contact between the specimen and the noble metal oxide by forming the dielectric material thin film or semiconducting material thin film 32 on the thin film 31 containing the noble metal oxide. The noble metal oxide can emit oxygen and oxidize other materials in some cases. For example, AgO is known as a strong oxidizing agent. Accordingly, if the specimen or a solvent including the specimen is brought into direct contact with the noble metal oxide, a chemical reaction between them can change them into other materials not included originally. As a result, such a case can take place in which detection of the material to be detected becomes difficult. According to the present invention, the thin film containing the noble metal oxide is coated with a dielectric or semiconductor transparent protection material thin film, which makes it possible to suppress such a chemical reaction and to achieve stable molecular sensing.

Furthermore, the dielectric material thin film or semiconducting material thin film 32 serves to protect the thin film 31 containing the noble metal oxide. The noble metal oxide dissolves readily in an acid or alkali in many cases. Besides, it dissolves in water though in only minute amounts. Since the thin film 31 containing the noble metal oxide has a thickness of about 1-500 nm originally, even dissolution in minute amounts can eliminate the film, thereby totally depriving the sensor of its sensitivity. Thus, selecting a stable dielectric material or semiconducting material for the specimen can suppress the dissolution of the noble metal oxide, and stabilize the sensing.

To the dielectric material or semiconducting material described above, any materials are applicable basically. However, to achieve the purpose of increasing the chemical stability of the sensor as described above, it is desirable that these materials be chemically stable. Considering this, as the dielectric material, a silicon oxide (including silica glass) or a nitride, a generally used glass material, or a polymer material such as acrylic, polycarbonate, polyethylene and polypropylene is preferable. As the semiconducting material, chemically stable Si or Ge, or a compound semiconductor is preferable. The semiconductor with high electrical conductivity, however, is likely to prevent the electric field enhancement due to plasmons, that is, the Raman scattering enhancement, from taking place. Accordingly, it is preferable that these materials exhibit electric property similar to that of an intrinsic semiconductor.

It is desirable to form the dielectric material thin film and semiconducting material thin film by the physical vapor deposition method or film deposition method in a vacuum just as the thin film containing the noble metal oxide. As the physical vapor deposition method, the sputtering method is desirable, and as the film deposition method in a vacuum, the vacuum vapor deposition method is desirable. In addition, as for materials capable of forming a thin film by spin coat, they can be applied to the surface of the thin film containing the noble metal oxide by the spin coat.

As for the thickness of the dielectric material thin film and semiconducting material thin film, 1-500 nm is preferable, and 10-200 nm is more preferable. If the film thickness is too thick, the electric field enhancement effect due to plasmons is lost. In contrast, if it is too thin, the wider bandwidth of the wavelength range of the excitation light for exciting the plasmons is insufficient.

Figure 12:
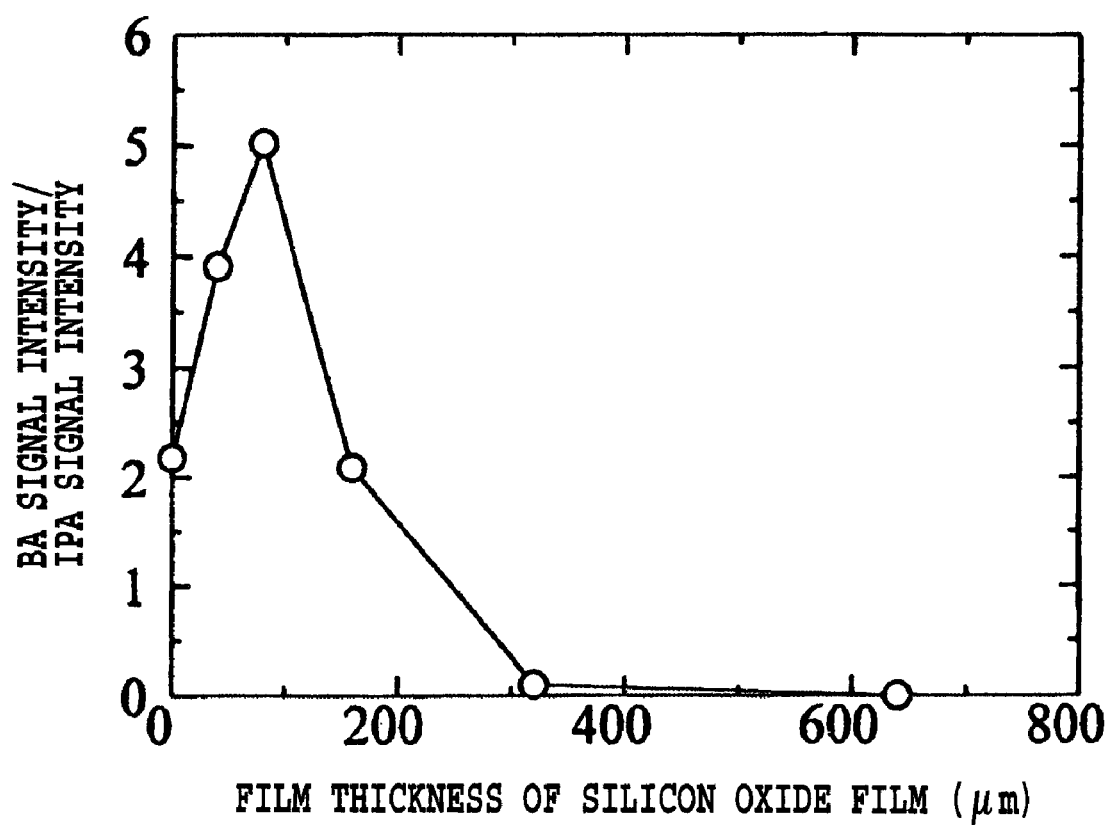
FIG. 12 is a graph illustrating relationships between the film thickness of a dielectric material layer formed on a chip and Raman scattered light intensity.

FIG. 12 illustrates results of actually confirming the effect. Here, the silver oxide was used as the noble metal oxide, and the silicon oxide thin film (silicon oxide film) was used as the dielectric material thin film. The specimen in this case was obtained by dissolving benzoic acid (BA) in 2-propanol (IPA). For the details, see example 2. It is found that a silicon oxide film of about 1-160 nm provides higher intensity of the signal as compared with a case without the silicon oxide film. However, a further increase of the thickness of the silicon oxide film reduces the signal as compared with the case without the silicon oxide film, and the film thickness of about 500 nm provides only a very minute signal. Furthermore, beyond 600 nm, the signal was not observed in the example 2. It goes without saying that when BA has a concentration higher than the specimen used in the example 2, it found that although the detection is possible, the highly sensitive detection of a minute amount of molecules is difficult.

On the other hand, the dielectric material thin film or semiconducting material thin film has an advantage of being able to suppress the chemical reaction between the specimen and the noble metal oxide. The advantage naturally increases with the film thickness. Consequently, when the specimen or solvent is a material that is likely to cause a reaction with the noble metal oxide, more highly sensitive observation eventually becomes possible by placing emphasis on the suppression of the chemical reaction at the cost of the detection sensitivity of the signal to some extent. In such a case, the film thickness of the silicon oxide film is preferably about 10-500 nm.

Considering the foregoing conditions, it is preferable that the film thickness of the dielectric material thin film or semiconducting material thin film is 1-500 nm, and particularly 10-200 nm to simultaneously achieve the high sensitivity enhancement of the signal and the suppression of the chemical reaction.

Several methods are enumerated of implementing the molecular sensing according to the Raman spectroscopic analysis using the above-mentioned chip for Raman scattering enhancement in accordance with the present invention.

A first method is as follows. Before carrying out the Raman spectroscopic analysis, the particles containing the noble metal are formed between the substrate and the dielectric material thin film or semiconducting material thin film by the reduction or decomposition of the noble metal oxide in the chip for Raman scattering enhancement. It is desirable to utilize the electromagnetic irradiation to form the particles. The wavelength of the electromagnetic wave used is not restricted in particular, but is appropriately determined in accordance with the noble metal oxide to be subjected to the reduction or decomposition. For example, as to the chip for Raman scattering enhancement using the silver oxide, the electromagnetic irradiation with various wavelengths from an ultraviolet region to infrared region can form the particles containing silver. Besides, the electromagnetic wave can be monochromatic light such as a laser beam or continuous spectrum light.

Figure 5A:
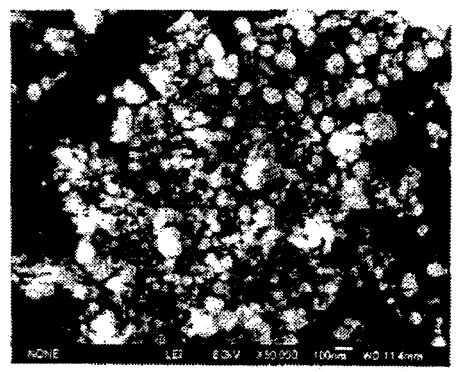
FIG. 5 is views showing SEM images of silver particles formed by laser beam irradiation of a silver oxide.
Figure 5B:
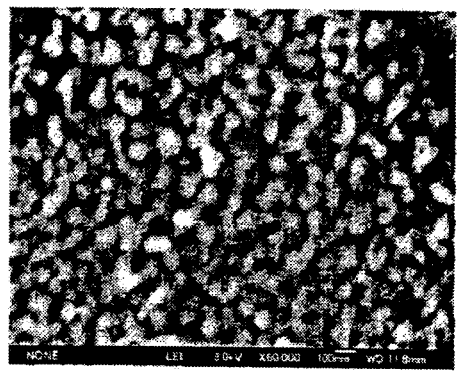
Figure 5C:
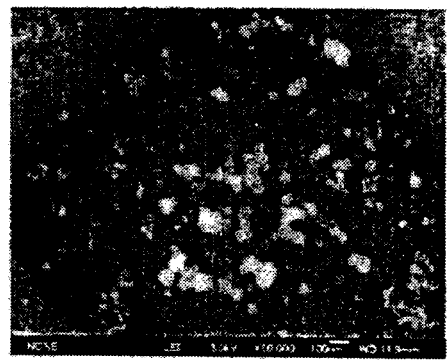
Figure 5D:
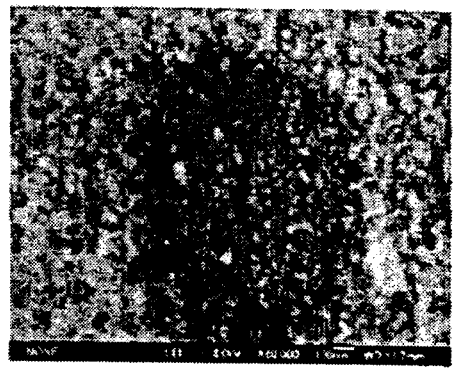

FIGS. 5(a)-5(d) show SEM (scanning electron microscopic) images of the silver particles when a 100 nm thick silver oxide thin film was irradiated with an Ar ion laser beam (wavelength 488 nm). Here, the silver oxide was formed by setting Ag as a target, and by applying the reactive sputtering method that uses a gas mixture of oxygen and Ar as a reactive gas. FIG. 5(a) was created by making the flow ratio $O_2/(Ar+O_2)$ between the oxygen and Ar 0.75; FIG. 5(b) by making the flow ratio 0.7; FIG. 5(c) by making the flow ratio 0.6; and FIG. 5(d) by making the flow ratio 0.5. The duration of the laser beam irradiation was five minutes for only the specimen of FIG. 5(a), and seven minutes for the others. The formation of aggregated particles can be confirmed at portions irradiated with the laser beam. The diameter of the particles is about 20-100 nm.

These SEM images are examples, and the particle diameters and particle distribution can vary according to the film thickness of the silver oxide, the oxygen content, the fabrication method and the irradiation duration of the laser. The SEM images shown here are photographed in the specimen without putting the dielectric material thin film or semiconducting material thin film. This is because if these films are put, the particles are formed in the films, and hence the observation with the SEM cannot be achieved.

Figure 6A:
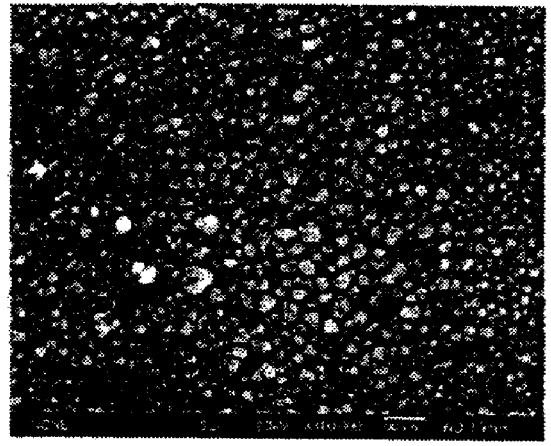
FIG. 6 is views showing SEM images when irradiating a silicon oxide film formed on the silver oxide with a laser beam.
Figure 6B:
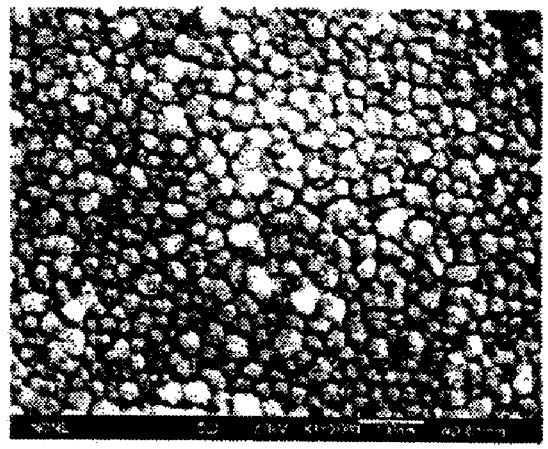

FIGS. 6(a) and 6(b) illustrate examples of SEM images when a chip for Raman scattering enhancement, which employs a silicon oxide film as the dielectric material thin film, is irradiated with an Ar ion laser beam. FIG. 6(a) shows an SEM image after the chip for Raman scattering enhancement, which has a 160 nm thick silicon oxide film formed on the silver oxide, is irradiated with the laser beam; and FIG. 6(b) shows an SEM image after the chip for Raman scattering enhancement, which has an 80 nm thick silicon oxide film formed on the silver oxide, is irradiated with the laser beam. Because of the presence of the silicon oxide film, the particles containing Ag cannot be confirmed. However, it is confirmed that asperities are created on the silicon oxide film surface at portions irradiated with the laser beam. The reason for this is considered that the particles containing Ag are formed internally, or that oxygen is emitted because of the decomposition or reduction of the silver oxide. However, the asperities on the silicon oxide film surface as illustrated in FIGS. 6(a) and 6(b) are not always observed. For example, when the silver oxide thin film is thin, or when the silicon oxide film is too thick or too thin, they are unobservable sometimes. In addition, when the amount of oxygen in the silver oxide is small, it is likely that the distinct asperities are not observed.

Apart from the electromagnetic irradiation, the particles containing the noble metal can be formed by heat treatment after constructing the chip for Raman scattering enhancement. As for heat treatment temperature, 100° C. or above is good for silver oxide, 500° C. or above is good for platinum oxide, and 700° C. or above is good for palladium oxide. As for the duration of the treatment, several minutes to several tens of minutes are desirable.

In the case of the silver oxide, efficient molecular detection effect has been confirmed when the particles were formed by carrying out the electromagnetic irradiation after the several minute heat treatment of the chip for Raman scattering enhancement at 50-300° C., preferably at 80-150° C. For example, when carrying out the Raman spectroscopic analysis using the Ar ion laser beam as the excitation light after performing the Ar ion laser beam irradiation after heating AgO at 100° C. for five minutes, the sensitivity was achieved of about 1.5-2 times higher than the case where the heat treatment was not performed. The details will be described later in an example 4.

As for the chip for Raman scattering enhancement, which has the particles containing the noble metal formed inside the dielectric material thin film or semiconducting material thin film by these methods, the specimen such as a solution or gas is brought into contact with or close to the surface of the chip to carry out the Raman spectroscopic analysis to perform the detection of the specimen.

However, the foregoing electromagnetic irradiation or heat treatment before the measurement is not always necessary. Such a method will be described below as a second method.

A second method is one that forms the particles containing the noble metal with the light from the light source used for the Raman spectroscopic analysis, and carries out the Raman scattering enhancement using the particles. In this method, the observation of the Raman spectroscopic analysis itself becomes the step of forming the particles. Accordingly, the foregoing step of the electromagnetic irradiation or heat treatment for forming the particles in advance can be omitted, thus enabling simpler sensing.

As the first method, the second method can increase the sensing sensitivity by carrying out heat treatment of the chip for Raman scattering enhancement at 50-300° C., preferably at 80-150° C., before the excitation light irradiation (that is, electromagnetic irradiation) in the Raman spectroscopic analysis.

In the method, however, the particles are gradually formed by irradiation with the excitation light used for the Raman spectroscopic analysis. Thus, the Raman scattering enhancement effect increases gradually, and hence the signal intensity increases with measurement time. Accordingly, to perform quantitative analysis, evaluation is made by measuring saturation values of the signal intensity, or from values the signal intensity reaches when a fixed time has elapsed from the start of the excitation light irradiation.

As for the electromagnetic irradiation for forming the particles as described above, and the excitation light irradiation for the Raman spectroscopic analysis, they can be carried out either from the substrate side or from the dielectric material thin film or semiconducting material thin film side. Besides the detection of the Raman scattered light can be made from either one of the sides. However, if the electromagnetic irradiation, the excitation light irradiation, or the detection of Raman scattered light is carried out from the substrate side to increase the sensitivity of sensing, it is preferable that the transmittance of the substrate is high for the electromagnetic wave, excitation light, or Raman scattered light. Likewise, if the electromagnetic irradiation, the excitation light irradiation, or the detection of Raman scattered light is carried out from the dielectric material thin film or semiconducting material thin film side, it is preferable that the transmittance of these thin films is high for the electromagnetic wave, excitation light, or Raman scattered light.

FIGS. 7(a)-7(h) show several examples of configurations of the chip for Raman scattering enhancement 17, which includes the substrate 30, the thin film 31 containing the metal oxide, and the dielectric material thin film or semiconducting material thin film 32; the specimen 16; the cell (container) 15 for containing the specimen; the incident direction of the excitation light 41; and the detection direction of the Raman scattered light 42.

FIG. 7(a) shows the same configuration as that shown in FIG. 1. First, the chip for Raman scattering enhancement 17 is placed on the bottom of the cell 15 for containing the specimen 16 in such a manner that the surface on which the molecular detecting element is formed comes to the top surface. The specimen 16 is put in the cell 15, the excitation light 41 is incident from the upper part, and the upward Raman scattered light 42 is observed. In this case, the specimen 16 consists of a solution or gas heavier than air.

FIG. 7(b) shows a configuration in which the cell 15 and the chip for Raman scattering enhancement 17 are placed as in FIG. 7(a), the excitation light 41 is incident from the upper part, and the downward Raman scattered light 42 is observed. In this case, the substrate 30 of the chip for Raman scattering enhancement 17 and the undersurface (bottom) of the cell 15 must be made of a material that can readily transmit the Raman scattered light 42.

FIG. 7(e) and FIG. 7(f) show examples in which the excitation light 41 is launched from the lower part in the same configurations as those of FIG. 7(a) and FIG. 7(b). In this case, the substrate 30 of the chip for Raman scattering enhancement 17 and the undersurface of the cell 15 must be made of a material that can readily transmit the excitation light 41. In addition, in FIG. 7(f), since the Raman scattered light 42 is also detected from the lower side, the substrate 30 of the chip for Raman scattering enhancement 17 and the undersurface of the cell 15 must be made of a material that can readily transmit the Raman scattered light 42 as well.

FIG. 7(c) and FIG. 7(d) show examples in which the thin film 31 containing the noble metal oxide and the dielectric material thin film or semiconducting material thin film 32 are formed on the bottom of the cell 15. In other words, the cell itself is used as the substrate for forming the chip for Raman scattering enhancement. In both FIG. 7(c) and FIG. 7(d), although the excitation light 41 is launched from the upper part, it is obvious that it can be launched from the lower part.

In addition, providing the cell 15 with a cap 37 as shown in FIG. 7(g) makes it easy to carry out observation even if the specimen 16 is a gas. Beside, as shown in FIG. 7(h), it is also possible to form inside the cap 37 the thin film 31 containing the noble metal oxide and the dielectric material thin film or semiconducting material thin film 32, and to use the cap as the substrate of the chip for Raman scattering enhancement.

It goes without saying that the irradiation with the excitation light and the detection of the Raman scattered light can be carried out either from the upper part of from the lower part. In addition, although the excitation light irradiation and Raman scattered light detection are performed in the vertical direction to the chip for Raman scattering enhancement, any angle can be used in practice. Besides, the cross sectional shape of the substrate and that of the cell are not necessarily rectangular. It is desirable that various shapes be selected according to the shape and application of the specimen.

The foregoing cell can be replaced by a flow channel. The molecular detection is possible with causing the specimen to flow through the flow channel by placing the chip for Raman scattering enhancement in the flow channel as described above, or by forming the chip for Raman scattering enhancement directly on the inner wall of the flow channel.

Although the foregoing description is made as to the method of forming a single layer of a single type of the dielectric material thin film or semiconducting material thin film on the single layer of a single type of the thin film containing the noble metal oxide, it is not indispensable that they are a single type or single layer. Rather than that, a combination of a plurality of layers can sometimes achieve higher detection sensitivity and stability.

Figure 8:
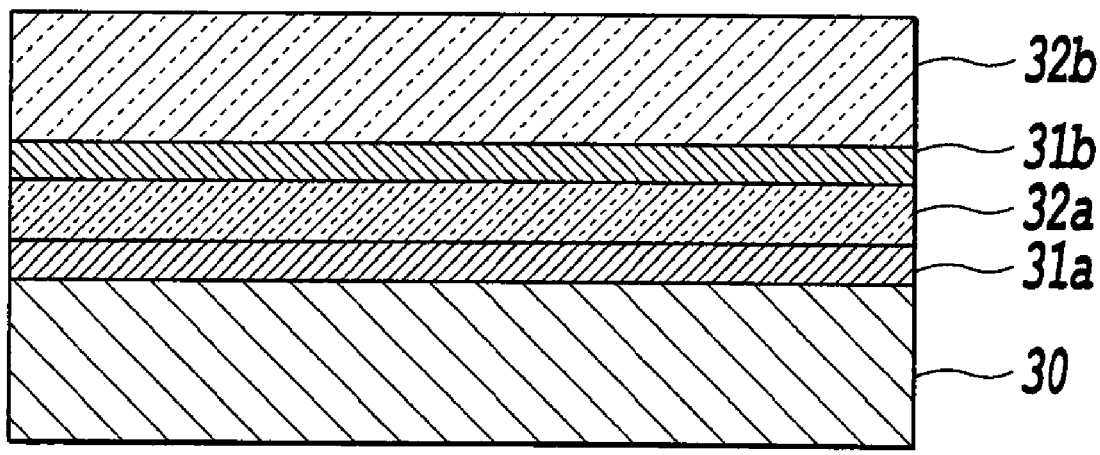
FIG. 8 is a schematic cross-sectional view showing another structure of the chip for Raman scattering enhancement in accordance with the present invention.

For example, when using the silver oxide thin film as the thin film containing the noble metal oxide and $SiO_2$ as the dielectric material thin film, in either case whether the film thickness of the silver oxide thin film is too thick or too thin, the Raman scattering enhancement effect is reduced. In view of this, by forming a silver oxide thin film layer with the optimum film thickness on a substrate, by further forming a $SiO_2$ layer on that, and by further forming a silver oxide thin film layer and $SiO_2$ layer on that, multi-layered particles containing silver with the optimum particle diameter are formed, thereby being able to obtain stronger Raman scattering enhancement, and to stabilize the sensor. FIG. 8 shows an example of such a chip for Raman scattering enhancement. The chip for Raman scattering enhancement shown in FIG. 8 has a structure in which on the substrate 30 are stacked a thin film 31a containing a first noble metal oxide, a first dielectric material thin film or semiconducting material thin film 32a, a thin film 31b containing a second noble metal oxide, and a second dielectric material thin film or semiconducting material thin film 32b.

Figure 9:
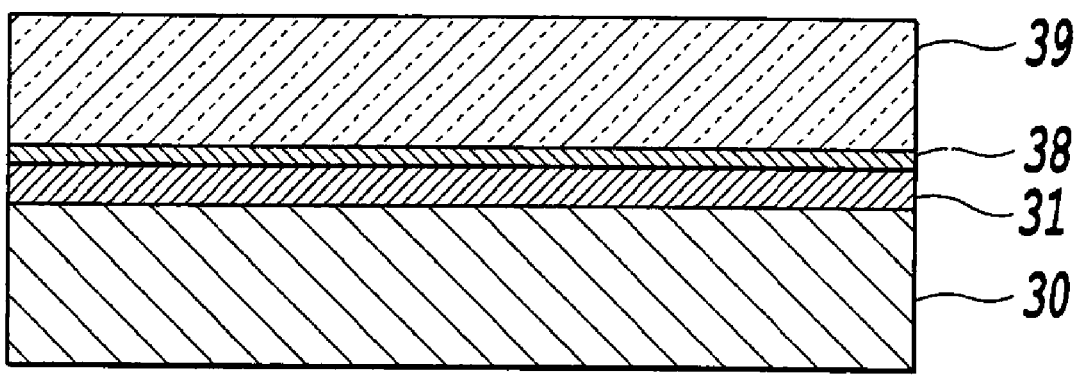
FIG. 9 is a schematic cross-sectional view showing still another structure of the chip for Raman scattering enhancement in accordance with the present invention.

In addition, the greater the refractive index of the dielectric material or semiconducting material formed around the particles containing the noble metal, the greater the variation of the wavelength range of the excitation light that provides efficient Raman scattering enhancement. Accordingly, it is preferable that the dielectric material or semiconducting material have a higher refractive index. However, such a material is not always easy to form on the thin film containing the noble metal oxide. For example, when depositing $TiO_2$ with a refractive index much higher than $SiO_2$ by a sputtering method, the deposition rate of $TiO_2$ becomes about one-fifth of the deposition rate of $SiO_2$, which is non-industrial. Accordingly, in such a case, it is better to form a thin $TiO_2$ layer on the thin film containing the noble metal oxide, and to further form a $SiO_2$ layer on that. FIG. 9 is a schematic diagram of such a chip for Raman scattering enhancement. The chip for Raman scattering enhancement as shown in FIG. 9 has a structure of stacking on the substrate 30 the thin film 31 containing the noble metal oxide, a $TiO_2$ thin film layer 38, and a $SiO_2$ thin film layer 39. It is enough for the $TiO_2$ thin film layer 38 to have a film thickness of about 1-20 nm.

When a Si layer is used as a high refractive index material, for example, since Si has large optical absorption in the visible light region, it is difficult for the irradiation or the Raman scattered light acquisition to be carried out from the Si layer side. Such a problem is also solved by forming a thin Si layer with a film thickness of about 1-20 nm, and by forming a $SiO_2$ layer thereon.

The combinations as described above are not limited to the foregoing examples. Any combinations are conceivable which stack in a multilayer fashion one or more layers of the thin film containing the noble metal oxide and one or more layers of the dielectric material thin film or semiconducting material thin film. It is preferable to select according to the type of the specimen and the mode of the specimen (such as to whether it is a gas, liquid or solid, or high temperature or low temperature, or highly reactive or lowly reactive).

The present invention will now be described more concretely by way of example below. However, the following concrete examples do not limit the scope of the present invention.

EXAMPLE 1

The present example shows a case where the layer containing the noble metal oxide is formed on the substrate, and the dielectric material thin film layer is further formed thereon. For comparison purposes, results are also shown when using a chip (comparative chip A) without the dielectric material thin film layer, and a chip (comparative chip B) with only the substrate.

As the substrate, a silicon substrate 1 cm square and 525 μm thick was used. As the layer containing the noble metal oxide, a silver oxide was used. The silver oxide was formed by the reactive sputtering method that set Ag as a target and used a gas mixture of oxygen and Ar as a reactive gas. In that case, the flow ratio $O_2/(Ar+O_2)$ between the oxygen and Ar was set at 0.75. The composition of the silver oxide formed includes Ag and O at a ratio of one to one, which means that it is AgO. Thus, the silver oxide thin film is referred to as an AgO thin film from now on. In addition, sputtering was carried out by a sputtering method that used Ar gas and set $SiO_2$ as a target to form a silicon oxide film serving as the dielectric material thin film on the AgO thin film. Thus the chip for Raman scattering enhancement was made. The film thickness of the AgO thin film was 50 nm, and the film thickness of the silicon oxide film was 80 nm.

The comparative chip A was made as a chip having an AgO thin film formed in the same conditions as described above on the same silicon substrate as described above. In addition, the comparative chip B was made as a chip having only the same silicon substrate as described above.

As the excitation light source for the Raman scattering measurement, an Ar ion laser (wavelength 488 nm) was employed. Since the present example uses a silicon substrate as the substrate, the excitation light cannot transmit from the substrate side. Accordingly, the irradiation with light was carried out from the side at which the thin film was formed. This configuration is the deposition as shown in FIG. 7(a). Here the particles containing silver were formed by using the excitation light source for the Raman scattering measurement, which meant that a method was adopted of forming the particles containing the silver simultaneously with the Raman scattering measurement. The excitation light intensity applied on the chip surface was 2.7 mW. The excitation light was gathered through the objective lens with a magnification of 50 and an NA of 0.55, and was applied to the chip. The Raman scattering measurement was observed from the start of the excitation light irradiation up to five minutes at every one minute interval.

As the specimen, a solution was used which dissolved BA in a solvent IPA by $1.0 \times 10^{-5}$ mol/l.

Figure 10:
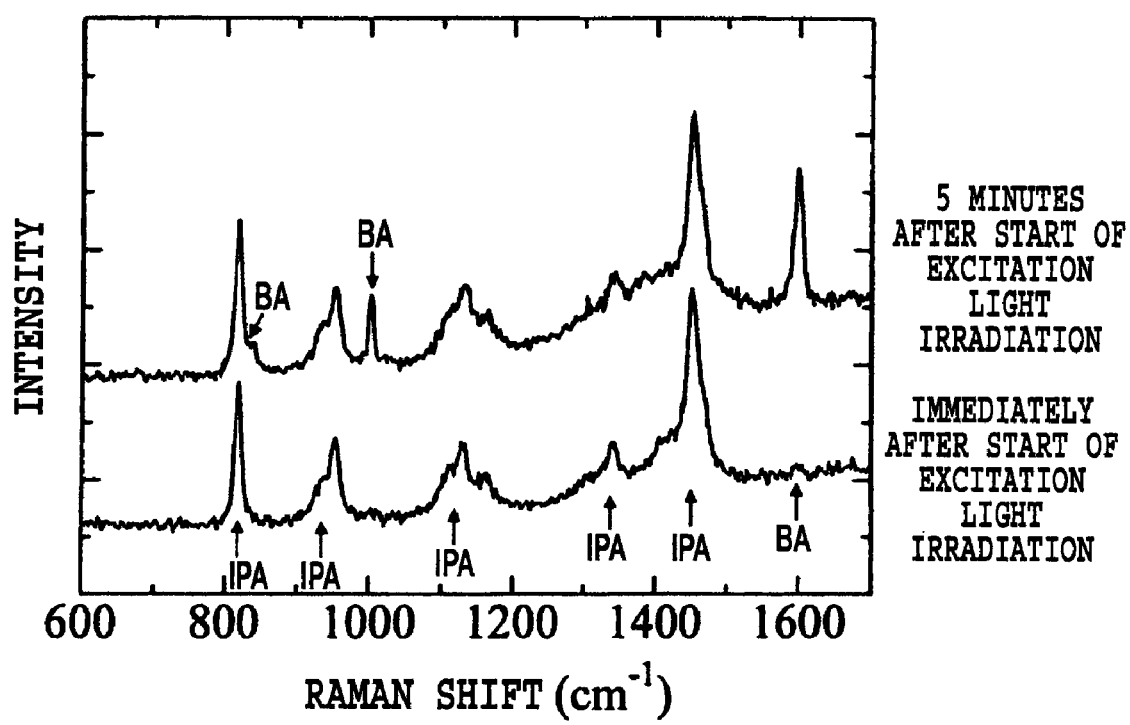
FIG. 10 is a diagram illustrating Raman scattering spectra measured using the chip for Raman scattering enhancement in accordance with the present invention.

FIG. 10 illustrates Raman scattering spectra of the specimen immediately after the excitation light irradiation and five minutes after the start of the excitation light irradiation when using the chip for Raman scattering enhancement in accordance with the present invention. It is found that although the signal due to BA is little observed immediately after the excitation light irradiation, the continuous excitation light irradiation thereafter increases the BA signal, which means that the Raman scattering enhancement takes place.

Figure 11:
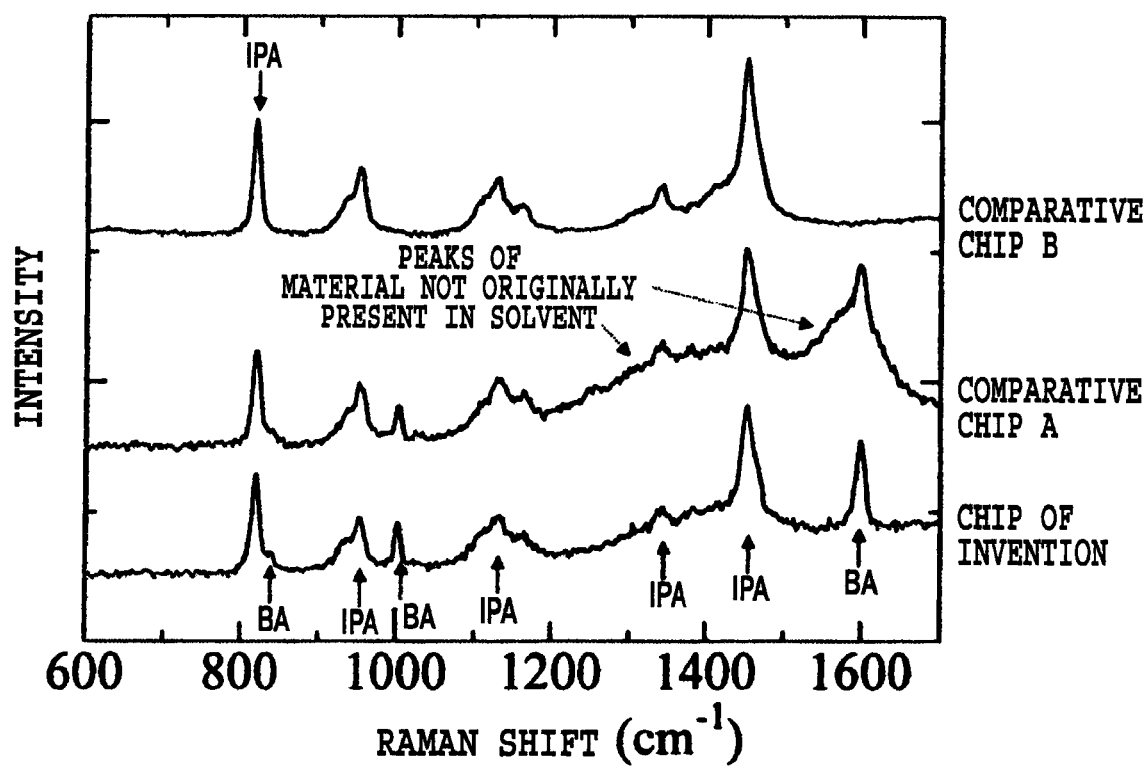
FIG. 11 is a diagram illustrating Raman scattering spectra measured using the chip for Raman scattering enhancement in accordance with the present invention and chips for comparison.

FIG. 11 illustrates Raman scattering spectra of the specimen detected by the chip for Raman scattering enhancement in accordance with the present invention and the comparative chips A and B. All of them are Raman scattering spectra five minutes after the start of the excitation light irradiation. The lowest spectrum is the Raman scattering spectrum when the chip for Raman scattering enhancement in accordance with the present invention is used. The middle one is the Raman scattering spectrum when the comparative chip A is used, and the uppermost one is the Raman scattering spectrum when the comparative chip B is used. It is found that the chip for Raman scattering enhancement in accordance with the present invention provides the Raman scattered light intensity due to BA about 1.5 times higher than the comparative chip A. In addition, as for the comparative chip B, although the signal of IPA, which is the solvent, is observed, none of the signal of BA is observed. In other words, it is not found that the comparative chip B brings about Raman scattering enhancement. It is found that thus using the chip for Raman scattering enhancement in accordance with the present invention makes it possible to detect the molecules dissolved in minute amounts at higher sensitivity.

Furthermore, in the Raman scattering spectrum measured using the comparative chip A, broad peaks due to a material that is not considered to be contained originally in the specimen are observed in a region of 1340-1600 $cm^{-1}$. They are considered to be a peak due to a material created by the chemical reaction between the AgO thin film and the solution. In contrast, such a peak is scarcely observed in the Raman scattering spectrum using the chip for Raman scattering enhancement in accordance with the present invention, but the peaks of the IPA and BA can be clearly observed. This means that the chip for Raman scattering enhancement in accordance with the present invention has the effect of preventing the chemical reaction between the specimen and the chip for Raman scattering enhancement. This effect enables stable and more highly accurate molecular observation of various solutions or gases.

EXAMPLE 2

By the same silver oxide thin film formative method as that of the example 1, an AgO thin film with a film thickness of 15 nm was formed on a silicon substrate. Then, five silicon oxide film layers with different film thicknesses of 40 nm, 80 nm, 160 nm, 320 nm and 640 nm were formed thereon to fabricate five chips. The silicon oxide film formative method was the same as that of the example 1. Besides, as a comparative chip, a chip was prepared which had the same AgO thin film but did not have the silicon oxide film layer.

As the specimen, a solution was used which dissolved BA in a solvent IPA by $1.0 \times 10^{-5}$ mol/l, and the Raman scattering measurement was carried out in the same configuration as that of FIG. 7($a$) as in the example 1. The present example employed a He—Ne laser (wavelength 633 nm) as the light source for the Raman scattering measurement. In this case also, the formation of the particles containing silver was performed using the light source for the Raman scattering measurement as in the example 1 so that the formation was carried out simultaneously with the Raman scattering measurement. The excitation light intensity irradiating the chip surface was about 1 mW. The excitation light was gathered through the objective lens with a magnification of 50 and an NA of 0.55, and was applied to the chip.

FIG. 12 illustrates the intensity of the BA signal measured using the individual chips. Here, the comparison is made using signal intensities observed after 9 minutes elapsed from the start of the excitation light irradiation. In addition, since this light source had variations in irradiation light intensity, it was difficult for the BA signal intensity itself to make accurate intensity comparison. Thus, the intensity of the BA signal observed at 1002 $cm^{-1}$ was divided by the IPA signal intensity observed at 820 $cm^{-1}$, thereby performing calibration of the signal intensity.

From FIG. 12, it is found that the chip whose silicon oxide film layer is 40 nm or 80 nm thick has the sensitivity greater than that of the comparative chip. As for the chip whose silicon oxide film layer is 160 nm thick, the signal intensity is nearly equal to that of the comparative chip. As for the chip whose film thickness is 320 nm, the signal becomes quite small, and when the film thickness is 620 nm, it is hardly observed. Thus, the Raman scattering intensity can be further enhanced by obtaining an optimum value for the film thickness of the dielectric layer (the silicon oxide film layer in the present example) of the chip for Raman scattering enhancement in accordance with the present invention experimentally or in a simulation.

However, even if the film thickness of the dielectric layer has an optimum value, there are some cases where the film thickness cannot suppress the chemical reaction completely. In such a case, even if the sensitivity is reduced to some extent, it is better to suppress the chemical reaction because it eventually enables more highly sensitive detection. It is desirable to determine the film thickness considering this fact.

EXAMPLE 3

By the same method as that of the example 1, the present example fabricated two types of chips for Raman scattering enhancement having the AgO thin film with a film thickness of 15 nm or 50 nm, and the Raman scattering measurement was performed for a solution that dissolved BA in a solvent IPA by $1.0 \times 10^{-5}$ mol/l in the configuration of FIG. 7($a$) as in the example 1. In the present example, an Ar ion laser (wavelength 488 nm and intensity 2.7 mW) was used as the light source for the Raman scattering measurement. The film thickness of the dielectric layer (silicon oxide film layer) of the chip for Raman scattering enhancement was made 80 nm. As for the formative method of the silicon oxide film and the formation of the particles containing silver, they were the same as those of the example 1.

As a result, as for the chip for Raman scattering enhancement having the AgO thin film with the film thickness of 15 nm, the peak intensity at 1002 $cm^{-1}$ due to BA after five minutes elapsed from the start of the excitation light irradiation was 430 counts. In contrast, as for the chip for Raman scattering enhancement having the AgO thin film with the film thickness of 50 nm, the peak intensity was 320 counts in the same conditions. Here, the term "counts" refers to a value proportional to the signal intensity detected with the photodetector (CCD) we used. In this way, high sensitivity can also be obtained by the optimization of the AgO film thickness.

However, the optimum thickness of the layer containing the noble metal oxide that provides the high intensity varies depending on the composition of the noble metal oxide and the dielectric material or semiconducting material formed thereon. Accordingly, it is preferable to optimize experimentally, or to optimize in a simulation with expecting the diameters of the formed particles containing the noble metal.

EXAMPLE 4

In the present example, the same chip for Raman scattering enhancement as that of the example 1 was fabricated. More specifically, on a silicon substrate were formed an AgO thin film with a film thickness of 50 nm and a silicon oxide film with a film thickness of 80 nm, and a 5-minute heat treatment was carried out at 100° C. in a nitrogen atmosphere before the Raman scattering measurement. In addition, as a comparative chip, a chip was prepared which was the same as that above except that it did not undergo the heat treatment.

With these chips, BA ($1.0 \times 10^{-5}$ mol/l) in a solvent IPA was measured in the configuration of FIG. 7($a$) as in the example 1 by using an Ar ion laser (wavelength 488 nm) as the excitation light source for Raman scattering measurement. The excitation light intensity irradiating the chip surface was 2.7 mW as in the example 1. The excitation light was gathered through the objective lens with a magnification of 50 and an NA of 0.55, and was applied to the chip. Although the present example carried out the formation of the particles containing silver using the light source for the Raman scattering measurement, it performed the foregoing irradiation processing separately before the measurement. The duration of the laser beam irradiation for forming the particles was five minutes.

Figure 13:
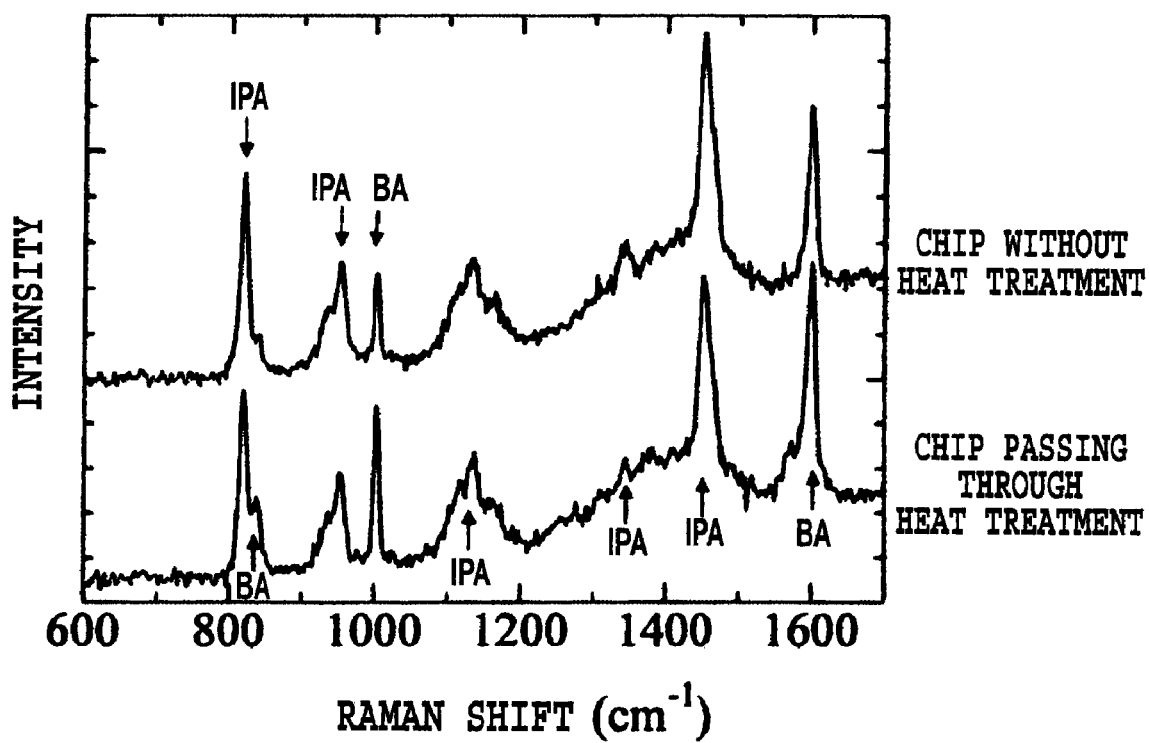
FIG. 13 is a graph illustrating measurement results of a chip subjected heat treatment and a chip not subjected to heat treatment.

FIG. 13 illustrates measurement results in the present example. The lower part spectrum of FIG. 13 was the measurement results of the chip passing through the heat treatment, and the upper part spectrum was the measurement results of the chip without passing through the heat treatment. It is found that the heat treatment can increase the BA detection sensitivity by a factor of about 1.7.

EXAMPLE 5

By the same fabrication method as that of the example 1, the present example fabricated on a silicon substrate an AgO thin film with a film thickness of 15 nm and a silicon oxide film with a film thickness of 80 nm. In addition, as a comparative chip, a chip without the silicon oxide film was prepared.

Figure 14:
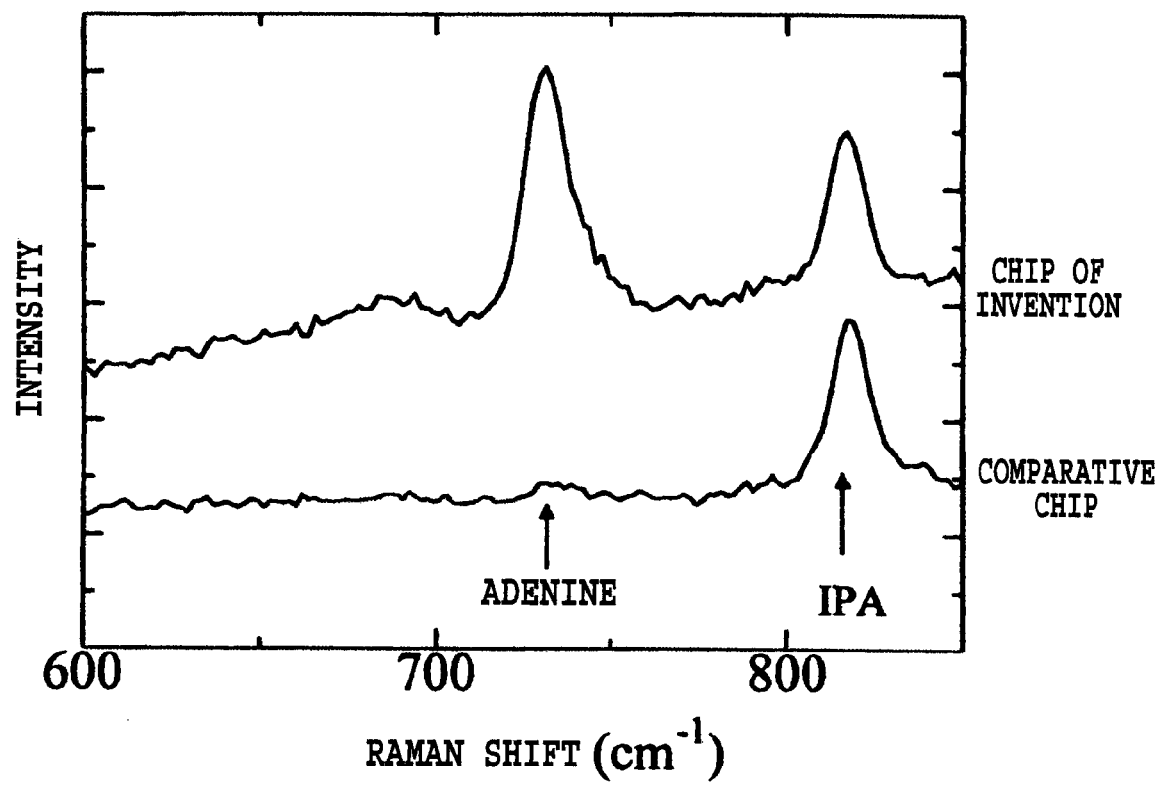
FIG. 14 is a diagram illustrating Raman scattering spectra of adenine dissolved in IPA.
Figure 15:
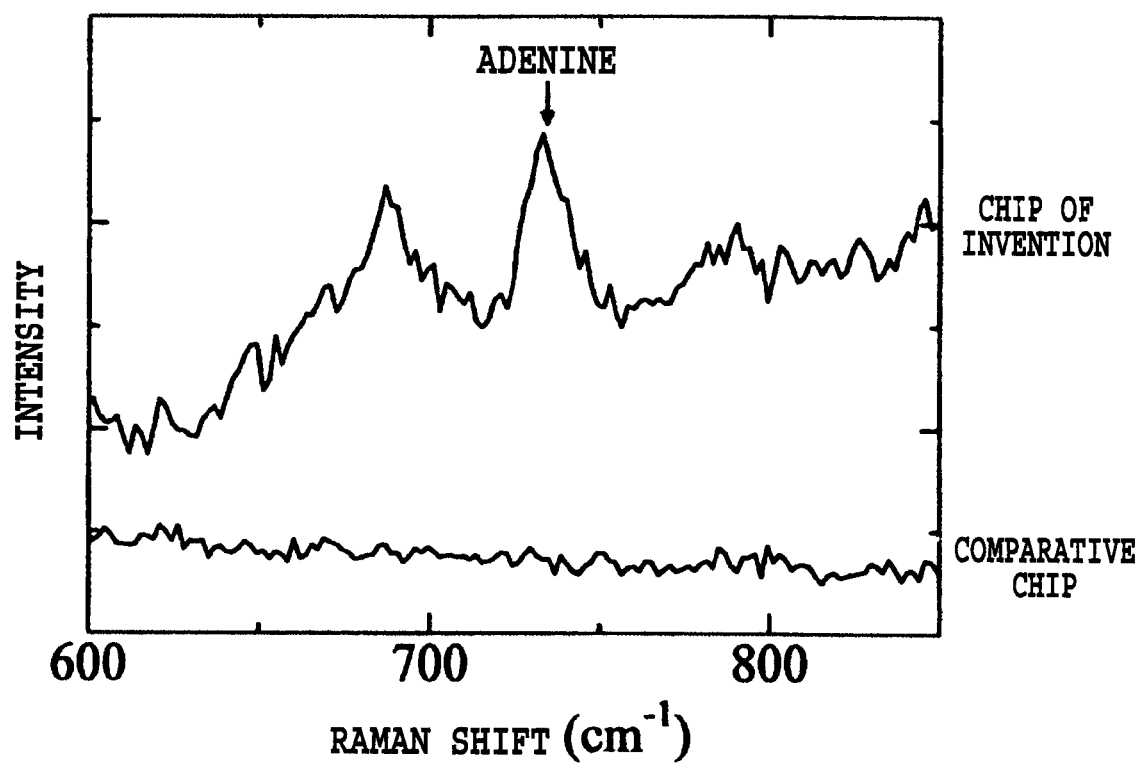
FIG. 15 is a diagram illustrating Raman scattering spectra of adenine dissolved in water.

With these chips, the Raman scattering measurement was carried out using as the specimen two types of solutions which dissolve adenine, one of the DNA bases, in a solvent IPA and water by $1.0 \times 10^{-5}$ mol/l, respectively. The measurement method was the same as that of the example 1. FIG. 14 illustrates Raman scattering spectra of the adenine dissolved in IPA, which was measured using the chip for Raman scattering enhancement in accordance with the present invention and the comparative chip; and FIG. 15 illustrates Raman scattering spectra of the adenine dissolved in the water. Either of these spectra is a signal observed nine minutes after the start of the excitation light irradiation.

Although the signal of the adenine is not observed when the comparative chip is used, the signal due to the adenine is observed when the chip for Raman scattering enhancement in accordance with the present invention is used. This shows that the detection of the adenine becomes possible by using the chip for Raman scattering enhancement in accordance with the present invention because it carries out the molecular detection at high sensitivity, and suppresses the decomposition of the adenine by repressing the chemical reaction between the AgO and adenine molecules.

EXAMPLE 6

The present example employed a 2-cm square, 0.5-mm thick $SiO_2$ glass as the substrate, and a silver oxide as the layer containing the noble metal oxide. The silver oxide was formed by a reactive sputtering method using Ag as a target and a gas mixture of oxygen and Ar as the reactive gas. In this case, the flow ratio $O_2/(Ar+O_2)$ between the oxygen and Ar was made 0.5. The composition of the silver oxide formed included Ag and O at a ratio of 2:1, which meant that it was $Ag_2O$. In practice, however, since the oxygen flow rate was small in this case, the composition was considered to be a mixture of AgO, $Ag_2O$, Ag and the like rather than uniform $Ag_2O$, and the ratio between Ag and O was 2:1 as a result. Thus, the layer is referred to as a "$Ag_2O$-containing layer" from now on. On the $Ag_2O$-containing layer, a silicon oxide film was formed in the same method as that of the example 1, thereby creating the chip for Raman scattering enhancement. The film thickness of the $Ag_2O$-containing layer was made 50 nm, and the film thickness of the silicon oxide film was made 80 nm.

With the foregoing chip for Raman scattering enhancement, the Raman spectroscopic analysis was carried out with applying the excitation light from the substrate side. The arrangement of the chip for Raman scattering enhancement, the specimen and the cell for containing the specimen had the configuration as shown in FIG. 7(h). A He—Ne laser (wavelength 633 nm) was used as the excitation light source for Raman scattering measurement, and BA ($1.0 \times 10^{-5}$ mol/l) in a solvent IPA was measured. The excitation light intensity applied to the surface of the chip for Raman scattering enhancement was 2.3 mW. The excitation light was gathered through the objective lens with a magnification of 50 and an NA of 0.55, and was applied to the chip for Raman scattering enhancement. As for the formation of the particles containing silver, it was carried out simultaneously with the Raman scattering measurement using the light source for the Raman scattering measurement as in the example 1.

Figure 16:
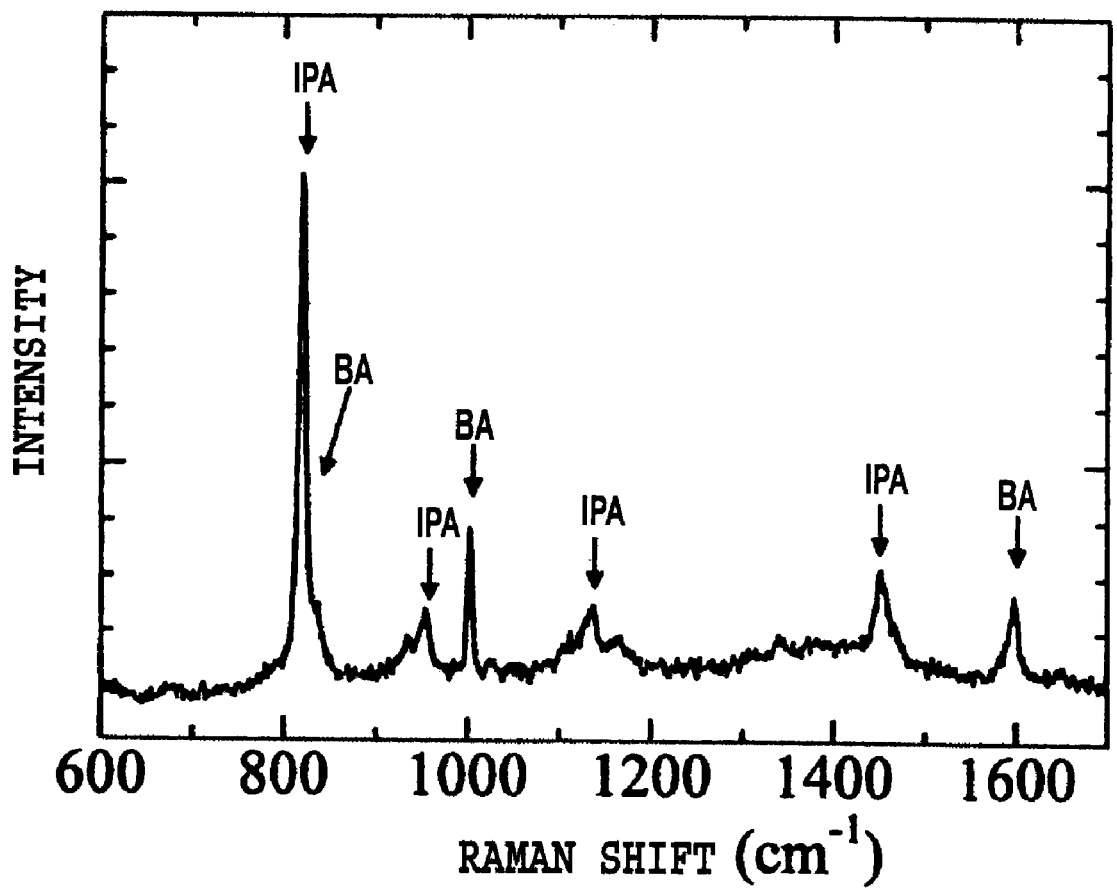
FIG. 16 is a diagram illustrating a Raman scattering spectrum measured using the chip for Raman scattering enhancement in accordance with the present invention.

FIG. 16 illustrates measurement results after nine minutes elapsed from the start of the excitation light irradiation. It shows that the present example also enables the detection of BA, and that it can reduce the peaks in the 1340-1600 $cm^{-1}$ region due to a material that is not considered to be contained originally, which are seen when the comparative chip A is used in the example 1.

EXAMPLE 7

The present example shows a case where the substrate itself consists of a metal, a case that employs a substrate having a dielectric material thin film layer formed on the surface of that metal substrate, or a case that employs a substrate having a metal thin film layer thereon.

The chips for Raman scattering enhancement fabricated are the following three types: chip 1, chip 2 and chip 3.

Chip 1: Composed of an aluminum plate serving as the substrate, an $Ag_2O$-containing layer with a film thickness of 50 nm, and a silicon oxide film layer with a film thickness of 80 nm formed thereon.

Chip 2: Composed of a substrate including an aluminum plate and a silicon oxide film layer with a film thickness of 20 nm formed thereon, an AgO layer with a film thickness of 50 nm, and a silicon oxide film layer with a film thickness of 80 nm formed thereon.

Chip 3: Composed of a substrate including a $SiO_2$ glass substrate and a silver layer with a thickness of 100 nm formed thereon, and an AgO layer with a film thickness of 50 nm, and a silicon oxide film layer with a film thickness of 80 nm formed thereon.

The above-mentioned AgO layer and $Ag_2O$-containing layer were formed in the same method as those of the foregoing example 1 and example 6. More specifically, in the reactive sputtering method placing Ag as a target and using a gas mixture of oxygen and Ar as the reactive gas, they were formed by setting the flow ratio $O_2/(Ar+O_2)$ between the oxygen and Ar at 0.75 when forming the AgO layer, and at 0.5 when forming the $Ag_2O$-containing layer. The silicon oxide film layer was formed by placing $SiO_2$ as a target and employing a sputtering method using Ar gas in any cases described above.

As the excitation light source for Raman scattering measurement, a He—Ne laser (wavelength 633 nm) was used. In addition, the arrangement of the chip for Raman scattering enhancement, specimen, and the cell for containing the specimen was that as shown in FIG. 7(a). The formation of the particles containing silver was carried out simultaneously with the Raman scattering measurement using the light source for the Raman scattering measurement. The excitation light intensity applied to the surface of the chip for Raman scattering enhancement was about 1 mW. The excitation light was gathered through the objective lens with a magnification of 50 and an NA of 0.55, and was applied to the chip for Raman scattering enhancement.

As the specimen, a solution is used which solves BA in a solvent IPA by $1.0 \times 10^{-5}$ mol/l.

Figure 17:
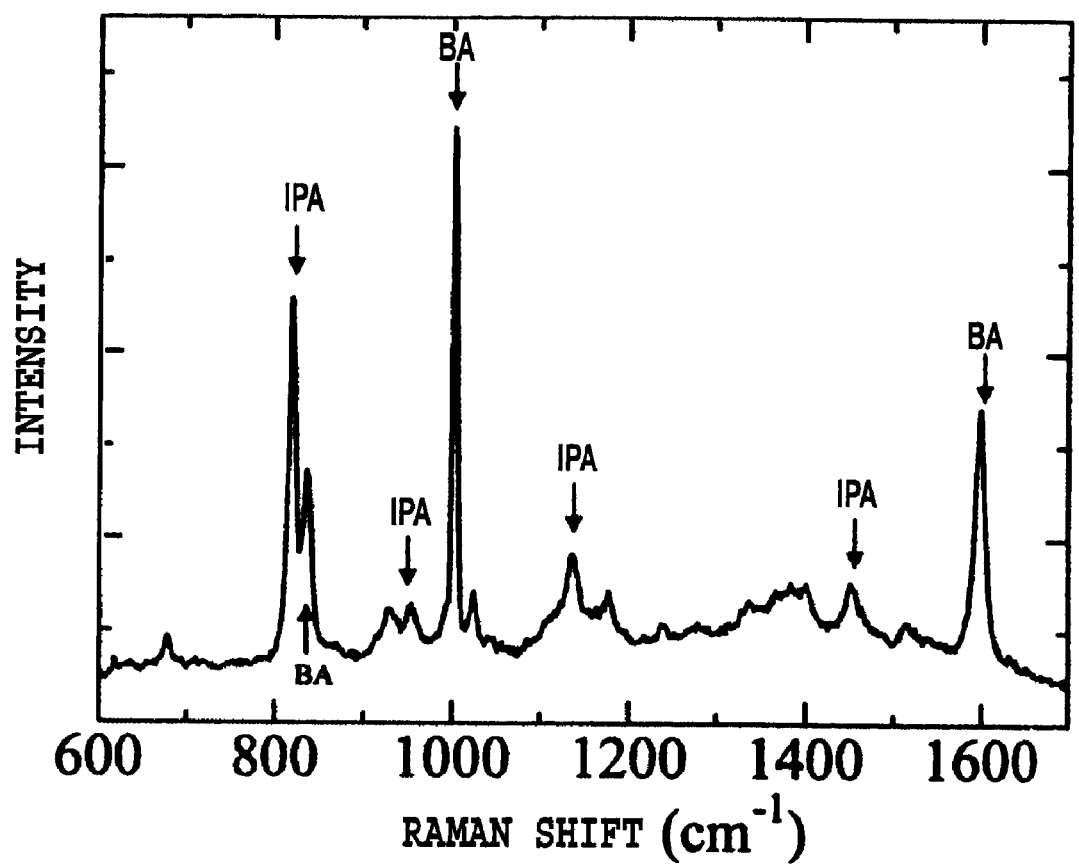
FIG. 17 is a diagram illustrating a Raman scattering spectrum measured using the chip for Raman scattering enhancement in accordance with the present invention.
Figure 18:
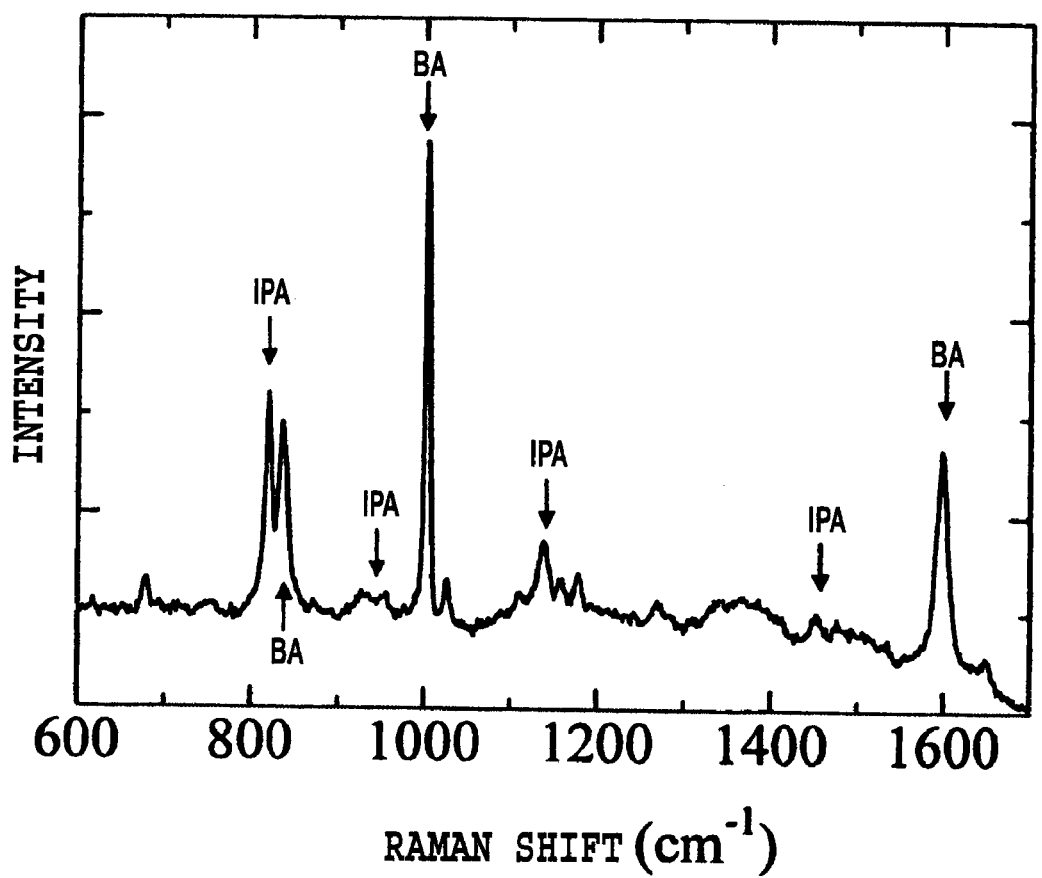
FIG. 18 is a diagram illustrating a Raman scattering spectrum measured using the chip for Raman scattering enhancement in accordance with the present invention.
Figure 19:
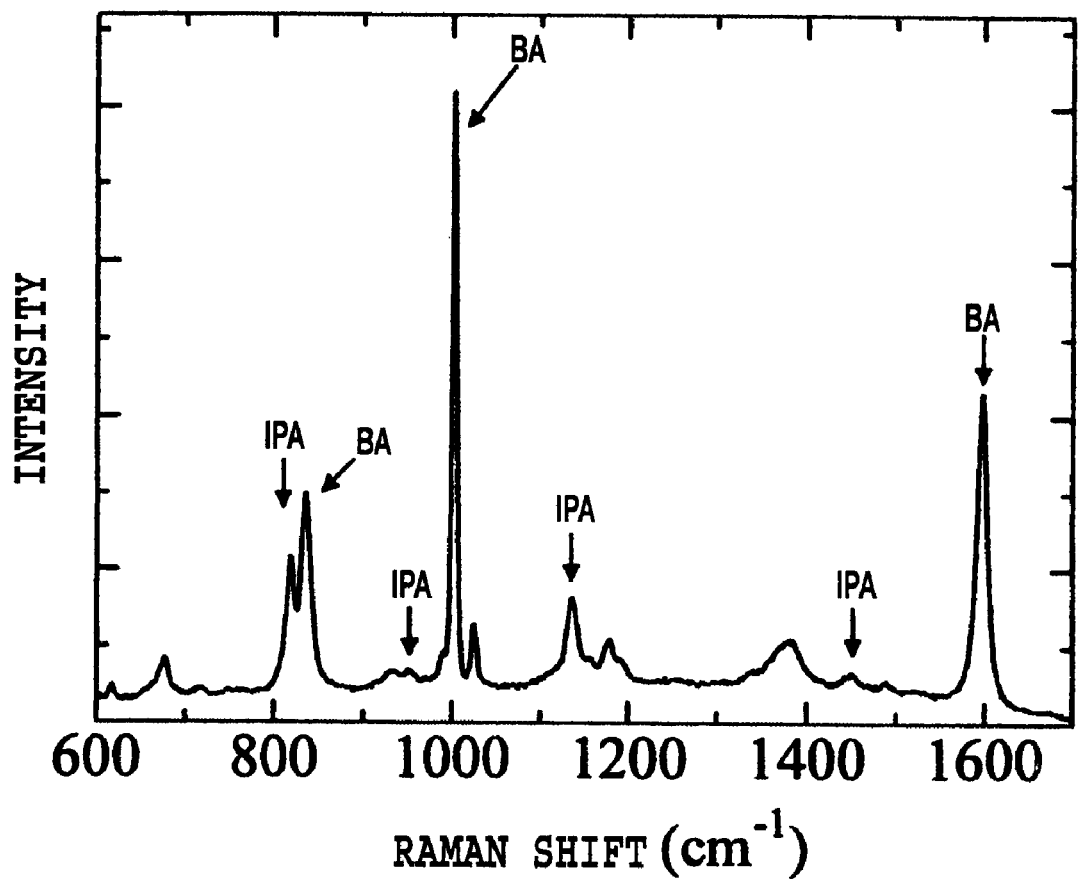
FIG. 19 is a diagram illustrating a Raman scattering spectrum measured using the chip for Raman scattering enhancement in accordance with the present invention.

FIGS. 17, 18 and 19 illustrate measurement results after nine minutes elapsed from the start of the excitation light irradiation of the chip 1, chip 2 and chip 3, respectively. In either specimens, the peaks due to BA are clearly observed, and the peaks are hardly observed in the 1340-1600 $cm^{-1}$ region, which are due to a material that is not considered to be contained originally and are seen when the comparative chip A of the example 1 is used.

Let us compare the intensities of the BA signals observed among these chips. In this case also, since there were variations in irradiation light intensity, it was difficult for the BA signal intensity itself to make accurate intensity comparison. In view of this, corrected values are obtained by dividing the intensity of the BA signal observed at 1002 $cm^{-1}$ by the IPA signal intensity observed at 820 $cm^{-1}$, so that the comparison is made by the corrected values. The corrected values are 1.4 for the chip A, 2.2 for the chip B and 4.6 for the chip C. Thus, employing the substrate having the dielectric material thin film layer formed on the surface of the metal substrate makes it possible to achieve higher sensitivity than using the metal substrate as it is, and to further increase the sensitivity by using a noble metal as the metal substrate.

EXAMPLE 8

The present example employed as its substrate a $SiO_2$ glass substrate 2 cm square and 0.5 mm thick; formed an AgO layer with a film thickness of 50 nm, a silicon oxide film layer with a film thickness of 20 nm, an AgO layer with a film thickness of 50 nm and a silicon oxide film layer with a film thickness of 80 nm in this order from below; and thus made a chip for Raman scattering enhancement. Here, the AgO layer was formed by the reactive sputtering method that set Ag as a target and used a gas mixture with a flow ratio $O_2/(Ar+O_2)$ between the oxygen and Ar of 0.75. In addition, the silicon oxide film layer was formed by the sputtering method that set $SiO_2$ as a target and used Ar gas.

A He—Ne laser (wavelength 633 nm) was used as the excitation light source for the Raman scattering measurement. The excitation light intensity irradiating the surface of the chip for Raman scattering enhancement was 2.3 mW. The excitation light was gathered through the objective lens with a magnification of 50 and an NA of 0.55, and was applied to the chip for Raman scattering enhancement. The arrangement of the chip for Raman scattering enhancement, the specimen and the cell for containing the specimen was the configuration as shown in FIG. 7(h). As for the formation of the particles containing silver, it was carried out simultaneously with the Raman scattering measurement using the light source for the Raman scattering measurement. As the specimen, a solution was used which dissolved BA in a solvent IPA by $1.0 \times 10^{-5}$ mol/l.

Figure 20:
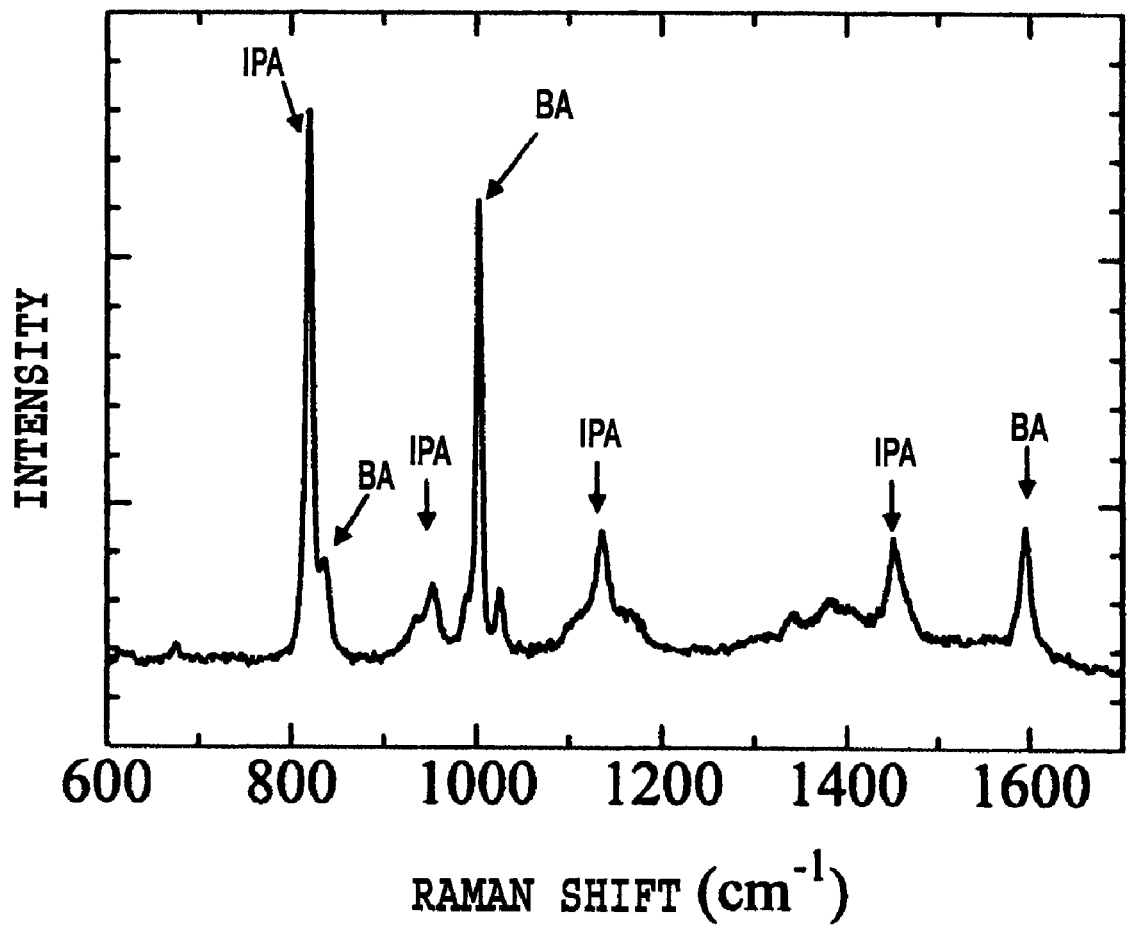
FIG. 20 is a diagram illustrating a Raman scattering spectrum measured using the chip for Raman scattering enhancement in accordance with the present invention.

FIG. 20 illustrates a measurement result using the chip for Raman scattering enhancement of the present example after 9 minutes elapsed from the start of the excitation light irradiation. In the present example, the BA signal can also be observed clearly, and the peaks in the 1340-1600 $cm^{-1}$ region are hardly observed, which are due to a material not considered to exist originally, and are seen when the comparative chip A of the example 1 is used.

EXAMPLE 9

In the present example, an AgO layer with a film thickness of 50 nm was formed on a 2 cm square $SiO_2$ glass substrate in the same method as the example 1; a Si layer with a film thickness of 5 nm was formed thereon as the semiconducting material thin film layer by the sputtering method that set Si as a target and used Ar gas; and an 80 nm silicon oxide film was formed thereon by the same method as that of the example 1, thereby making a chip for Raman scattering enhancement.

An Ar ion laser (wavelength 488 nm) was used as the excitation light source for Raman scattering measurement. The excitation light intensity applied to the surface of the chip for Raman scattering enhancement was 2.7 mW. The excitation light was gathered through the objective lens with a magnification of 50 and an NA of 0.55, and was applied to the chip for Raman scattering enhancement. The arrangement of the chip for Raman scattering enhancement, the specimen and the cell for containing the specimen was the configuration as shown in FIG. 7(a). As for the formation of the particles containing silver, it was carried out simultaneously with the Raman scattering measurement using the light source for the Raman scattering measurement. As the specimen, a solution was used which dissolved BA in a solvent IPA by $1.0 \times 10^{-5}$ mol/l.

Figure 21:
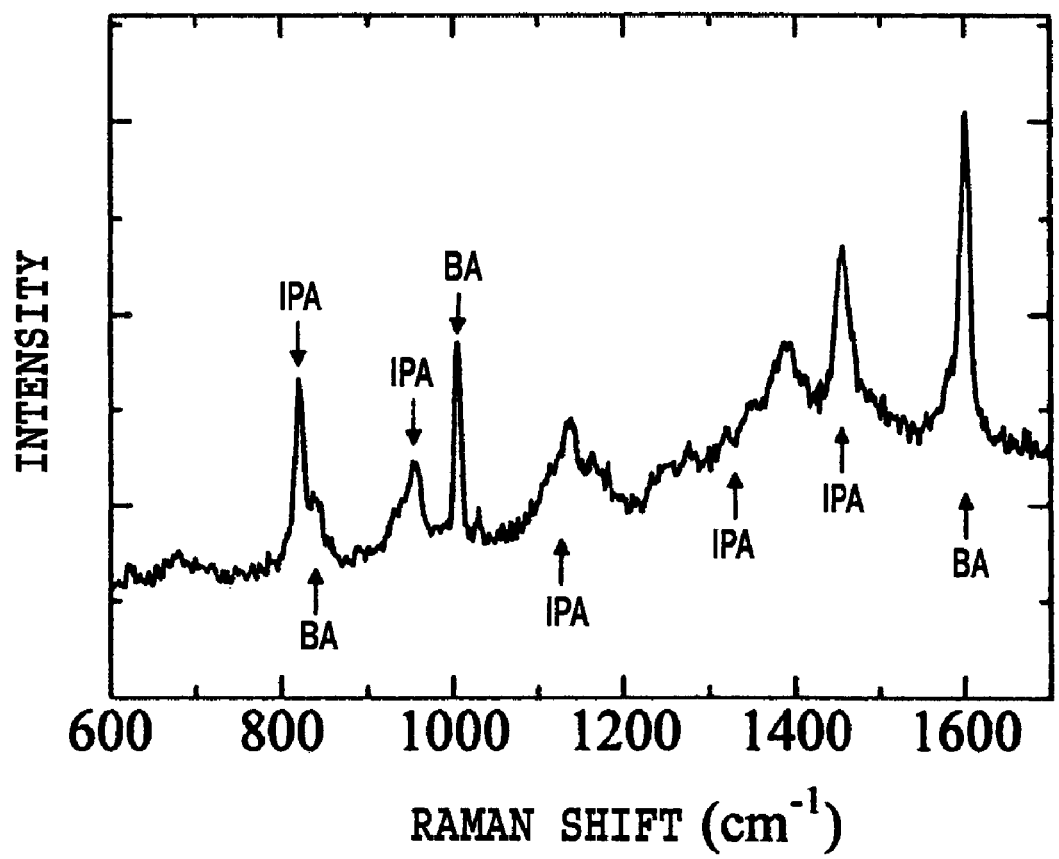
FIG. 21 is a diagram illustrating a Raman scattering spectrum measured using the chip for Raman scattering enhancement in accordance with the present invention.

FIG. 21 illustrates a measurement result using the chip for Raman scattering enhancement of the present example after 5 minutes elapsed from the start of the excitation light irradiation. In the present example, the BA signal can also be observed clearly, and the appearance of the peaks observed in the 1340-1600 $cm^{-1}$ region is suppressed, which are due to a material not considered to exist originally, and are seen when the comparative chip A of the example 1 is used. Thus using the chip for Raman scattering enhancement in accordance with the present invention enables stable molecular observation of a variety of solutions and gases.

What is claimed is:

1. A chip for Raman scattering enhancement for enhancing Raman scattering generated from a specimen by excitation light irradiation, said chip comprising:
   a thin film containing a noble metal oxide; and
   a dielectric material thin film or semiconducting material thin film formed thereon, wherein the noble metal oxide layer and the dielectric material thin film or semiconducting material thin film are built in a multilayer fashion.

2. The chip for Raman scattering enhancement as claimed in claim 1, wherein said noble metal oxide is a silver oxide, and the dielectric material thin film or semiconducting material thin film is a transparent protection material thin film.

3. The chip for Raman scattering enhancement as claimed in claim 1, wherein said thin film containing the noble metal oxide is formed on a substrate surface by a physical vapor deposition method or film deposition method in a vacuum.

4. A chip for Raman scattering enhancement for enhancing Raman scattering generated from a specimen by excitation light irradiation, said chip comprising:
   a substrate;
   a thin film containing a noble metal oxide formed on a surface of the substrate; and
   a dielectric thin film or semiconducting material thin film on the thin film containing a noble metal oxide,
   wherein said substrate has on its surface, on which said thin film containing the noble metal oxide is formed, a metal layer or a layer containing metal particles and wherein said thin film containing the noble metal oxide is formed on the substrate surface by a physical vapor deposition method or film deposition method in a vacuum.

5. The chip for Raman scattering enhancement as claimed in claim 3, wherein said substrate is substantially composed of a metal.

6. The chip for Raman scattering enhancement as claimed in claim 4, wherein said metal is a noble metal.

7. The chip for Raman scattering enhancement as claimed in claim 4, wherein said substrate has, on a top surface of said metal portion of its surface, a dielectric material thin film or semiconducting material thin film.

8. The chip for Raman scattering enhancement as claimed in claim 1, wherein said thin film containing the noble metal oxide contain noble metal particles resulting from deoxidization of the noble metal oxide.

9. The chip for Raman scattering enhancement as claimed in claim 1, wherein said dielectric material thin film or semiconducting material thin film has a film thickness from 1 nm to 500 nm inclusive.

10. The chip for Raman scattering enhancement as claimed in claim 1, wherein said dielectric material thin film or semiconducting material thin film is formed on the surface of said thin film containing the noble metal oxide by a physical vapor deposition method or film deposition method in a vacuum.

11. The chip for Raman scattering enhancement as claimed in claim 1, wherein said dielectric material thin film is a silicon oxide films.

12. The chip for Raman scattering enhancement as claimed in claim 1, wherein said semiconducting material thin film is silicon.

13. A molecular sensing device comprising:
   a chip for Raman scattering enhancement as defined in any one of claims 1-10 and 11-12;
   an excitation light source; and
   a detector for detecting Raman scattered light enhanced by said chip for Raman scattering enhancement.

14. The chip for Raman scattering enhancement as claimed in claim 4, wherein said substrate is substantially composed of a metal.

15. The chip for Raman scattering enhancement as claimed in claim 4, wherein said thin film containing the noble metal oxide contains noble metal particles resulting from deoxidization of the noble metal oxide.

16. A chip for Raman scattering enhancement for enhancing Raman scattering generated from a specimen by excitation light irradiation, said chip comprising:
   a plurality of thin films, each thin film containing a noble metal oxide; and
   a plurality of dielectric thin films or semiconductor thin films arranged in a stack so as to alternate with the thin films containing a noble metal oxide.

* * * * *

UNITED STATES PATENT AND TRADEMARK OFFICE
CERTIFICATE OF CORRECTION

PATENT NO. : 7,692,787 B2
APPLICATION NO. : 11/883405
DATED : April 6, 2010
INVENTOR(S) : Makoto Fujimaki, Junji Tominaga and Yasuhiko Iwanabe It is certified that error appears in the above-identified patent and that said Letters Patent is hereby corrected as shown below:

Title Page, Col. 2, Other Publications, delete "enchanced" and insert -- enhanced --.

Signed and Sealed this

Third Day of August, 2010

David J. Kappos
*Director of the United States Patent and Trademark Office*